US009114151B2

(12) United States Patent
Dudley, Jr.

(10) Patent No.: US 9,114,151 B2
(45) Date of Patent: Aug. 25, 2015

(54) METHOD FOR MODULATING OR CONTROLLING SODIUM CHANNEL CURRENT BY REACTIVE OXYGEN SPECIES (ROS) ORIGINATING FROM MITOCHONDRIA

(75) Inventor: Samuel C. Dudley, Jr., Chicago, IL (US)

(73) Assignees: THE UNITED STATES OF AMERICA DEPT. OF VETERANS AFFAIRS, Washington, DC (US); THE BOARD OF TRUSTEES OF THE UNIV. OF ILLINOIS, Urbana, IL (US)

(*) Notice: Subject to any disclaimer, the term of this patent is extended or adjusted under 35 U.S.C. 154(b) by 0 days.

(21) Appl. No.: 12/929,786

(22) Filed: Feb. 16, 2011

(65) Prior Publication Data

US 2011/0144192 A1  Jun. 16, 2011

Related U.S. Application Data

(63) Continuation-in-part of application No. 12/289,005, filed on Oct. 17, 2008, now Pat. No. 8,003,324.

(60) Provisional application No. 60/960,883, filed on Oct. 18, 2007, provisional application No. 61/305,668, filed on Feb. 18, 2010.

(51) Int. Cl.
*A61K 31/35* (2006.01)
*C12N 5/07* (2010.01)
*A61K 31/194* (2006.01)
*A61P 9/06* (2006.01)
*A61K 31/7084* (2006.01)

(52) U.S. Cl.
CPC ........... *A61K 31/7084* (2013.01); *A61K 31/194* (2013.01); *A61K 31/35* (2013.01)

(58) Field of Classification Search
CPC .. A61K 31/194; A61K 31/35; A61K 31/7084
See application file for complete search history.

(56) References Cited

U.S. PATENT DOCUMENTS

| 5,668,114 | A | 9/1997 | Birkmayer | |
|---|---|---|---|---|
| 5,849,732 | A * | 12/1998 | Suzuki et al. | 514/217.11 |
| 6,339,073 | B1 | 1/2002 | Pero | |
| 6,833,371 | B2 | 12/2004 | Atkinson et al. | |
| 7,094,600 | B2 | 8/2006 | Wang | |
| 7,226,950 | B2 | 6/2007 | Choi et al. | |
| 8,003,324 | B2 | 8/2011 | Dudley, Jr. | |
| 2004/0091477 | A1* | 5/2004 | Haines et al. | 424/144.1 |
| 2005/0202093 | A1 | 9/2005 | Kohane et al. | |
| 2006/0281668 | A1 | 12/2006 | Parobok et al. | |
| 2007/0212723 | A1 | 9/2007 | Dudley et al. | |
| 2008/0032940 | A1* | 2/2008 | Kalyanaraman et al. | 514/34 |
| 2008/0075666 | A1 | 3/2008 | Dudley, Jr. et al. | |
| 2011/0288044 | A1 | 11/2011 | Dudley, Jr. | |
| 2012/0288486 | A1 | 11/2012 | Dudley, Jr. | |
| 2012/0289482 | A1 | 11/2012 | Dudley, Jr. | |
| 2012/0308542 | A1 | 12/2012 | Dudley, Jr. | |

FOREIGN PATENT DOCUMENTS

| WO | WO 96/19225 A1 | 6/1996 |
|---|---|---|
| WO | WO 2007/098065 A1 | 8/2007 |
| WO | WO 2010/129964 A1 | 11/2010 |

OTHER PUBLICATIONS

Liu et al. (2010) A Central Role for Mitochondria in the Regulation of Cardiac Sodium Current. 2010 Biophysical Society Meeting Abstracts. Biophysical Journal, Supplement, Abstract. p. 7a.*
http://www.biophysics.org/2010meeting/Registration/RatesDeadlines/tabid/675/Default.aspx.*
Brugada P, Brugada J. Right bundle branch block, persistent ST segment elevation and sudden cardiac death: a distinct clinical and electrocardiographicsyndrome. A multicenter report. *J Am Coll Cardiol.* 1992;20:1391-1396. Kadish, a. et al. 2006. Patients with recently diagnosed nonischemic cardiomyopathy benefit from implantable cardioverter-defbrillators. J. Am Coll. Cardiol. 47:2477-2482. Amin As, Verkerk Ao, Bhuiyan Za, Wilde Aam, Tan Hl. Novel Brugada syndromcausing mutation in ion-conducting pore of cardiac Na channel does not affect ion selectivity properties. Acta Physiol Scand. 2005;185:291-301. Baroudi G, Napolitano C, Priori Sg, Del Bufalo a, Chahine M. Loss of function associated with novel mutations of the SCN5A gene in patients with Brugada syndrome. Can J Cardiol. 2004;20:425— 430. Baroudi G, Acharfi S, Larouche C, Chahine M. Expression and Intracellular localization of an SCN5A double mutant R1232W/T1620M implicated in Brugada syndrome. Circ Res. 2002;90:el 1— e16.
Kadish, A. et al. 2006. Patients with recently diagnosed nonischemic cardiomyopathy benefit from implantable cardioverter-defibrillators. *J. Am Coll. Cardiol.* 47:2477-2482.
Amin AS, Verkerk AO, Bhuiyan ZA, Wilde AAM, Tan HL. Novel Brugada syndrom-causing mutation in ion-conducting pore of cardiac Na_ channel does not affect ion selectivity properties. *Acta Physiol Scand.* 2005;185:291-301.
Baroudi G, Napolitano C, Priori SG, Del Bufalo A, Chahine M. Loss of function associated with novel mutations of the SCN5A gene in patients with Brugada syndrome. *Can J Cardiol.* 2004;20:425-430.
Baroudi G, Acharfi S, Larouche C, Chahine M. Expression and Intracellular localization of an SCN5A double mutant R1232W/T1620M implicated in Brugada syndrome. *Circ Res.* 2002;90:e11-e16.
Baroudi G, Pouliot V, Denjoy I, Guicheney P, Shrier A, Chahine M. Novel mechanism for Brugada syndrome: Defective surface localization of an SCN5A mutant (R1432G). *Circ Res.* 2001;88:e78-e83.
Vatta M, Dumaine R, Antzelevitch C, Brugada R, Li H, Bowles NE, Nademanee K, Brugada J, Brugada P, Towbin JA. Novel mutations in domain I of SCN5A cause Brugada syndrome. *Mol Genet Metab.* 2002;75:317-324.

(Continued)

*Primary Examiner* — Doug Schultz
(74) *Attorney, Agent, or Firm* — Dinesh Agarwal, P.C.

(57) ABSTRACT

Method for modulating or controlling sodium channel current of a cell includes inducing mitochondrial reactive oxygen species (ROS) production in the cell.

7 Claims, 6 Drawing Sheets

(56) References Cited

OTHER PUBLICATIONS

London B, Michalec M, Mehdi H, Zhu X, Kerchner L, Sanyal S, Viswanathan PC, Pfahnl AE, Shang LL, Madhusudanan M, Baty CJ, Lagana S, Aleong R, Gutmann R, Ackerman MJ, McNamara DM, Weiss R, Dudley SC Jr. Mutation in glycerol-3-phosphate dehydrogenase 1-like gene (GPD1-L) decreases cardiac Na_ current and causes inherited arrhythmias. *Circulation.* 2007;116:2260-2268.

Van Norstrand DW, Valdivia CR, Tester DJ, Ueda K, London B, Makielski JC, Ackerman MJ. Molecular and functional characterization of novel glycerol-3-phosphate dehydrogenase 1 like gene (GPD1-L) mutations in sudden infant death syndrome. *Circulation.* 2007;116:2253-2259.

Shen, W. et al. 2006. Involvement of glycerol-3-phosphate dehydrogenase in modulating the NADH/NAD+ ratio provides evidence of a mitochondrial glycerol-3-phosphate shuttle in *Arabidopis. Plant Cell.* 18:422-441.

Papadatos GA, Wallerstein PMR, Head CEG, Ratcliff R, Brady PA, Benndorf K, Saumarez RC, Trezise AEO, Huang CLH, Vandenberg JI, Colledge WH, Grace AA. Slowed conduction and ventricular tachycardia after targeted disruption of the cardiac sodium channel gene SCN5a. *Proc Natl Acad Sci U S A.* 2002;99:6210-6215.

Knollmann BC, Schober T, Petersen AO, Sirenko SG, Franz MR. Action potential characterization in intact mouse heart: steady-state cycle length dependence and electrical restitution. *Am J Physiol Heart Circ Physiol.* 2007;292:H614-H621.

Killeen MJ, Thomas G, Gurugin IS, Goddard CA, Fraser JA, Mahaut-Smith MP, Colledge WH, Grace AA, Huang CLH. Arrhythmogenic mechanisms in the isolated perfused hypokalaemic murine heart. *Acta Physiol.* 2007;189:33-46.

Zalba, G. et al. 2000. Vascular NADH/NADPH oxidase is involved in enhanced superoxide production in spontaneously hypertensive rats. *Hypertension.* 35:1055-1061.

Javesghani, D. et al. 2002. Molecular characterization of a superoxide-generating NAD(P)H oxidase in the ventilator muscles. *Am. J. Respir. Crit. Care Med.* 165: 412-418.

Zicha, S. Maltsev, V.A., Nattel, S., Sabbah, H.N. and Undrovinas, A.L. 2004. Posttranscriptional alterations in the expression of cardiac Na+ channel subunits in chronic heart failure. *J. Mol. Cell. Cardiol.* 37: 91-100.

Schreibmayer W, Dascal N, Lotan I, Wallner M, Weigl L. Molecular mechanism of protein kinase C modulation of sodium channel_-subunits expressed in *Xenopus oocytes. FEBS Lett.* 1991;291:341-344.

Ward, C.A., and Giles, W.R. 1997. Ionic mechanism of the effects of hydrogen peroxide in rat ventricular myocytes. *J. Physiol.* 500: 631-642.

Takeishi, Y., Jalili, T., Ball, N.A. and Walsh, R.A. 1999. Responses of cardiac protein kinase C isoforms to distinct pathological stimuli are differently regulated. *Circ. Res.* 85: 264-271.

Sharma, A. and Singh, M. 2001. Protein kinase C activation and cardioprotective effect of preconditioning with oxidative stress in isolated rat heart. *Mol. Cell. Biochem.* 219: 1-6.

Brawn, M.K., Chiou, W.J. and Leach, K.L. 1995. Oxidant-induced activation of protein kinase C in UC11Mg cells. *Free Radic. Res.* 22: 23-37.

Pfahnl AE, Viswanathan PC, Weiss R, Shang LL, Sanyal S, Shusterman V, Kornblit C, London B, Dudley SC Jr. A sodium channel pore mutation causing Brugada syndrome. *Heart Rhythm.* 2007;4:46-53.

Kyndt, F. et al. 2001. Novel SCN5A mutation leading either to isolated cardiac conduction defect or Brugada syndrome in a large French family. *Circulation.* 104:3081-3086.

Tipparaju SM, Saxena N, Liu SQ, Kumar R, Bhatnagar A. Differential regulation of voltage-gated K_ channels by oxidized and reduced pyridine nucleotide coenzymes. *Am J Physiol Cell Physiol.* 2005;288: C366-C376.

Tipparaju SM, Liu SQ, Barski OA, Bhatnagar A. NADPH binding to_-subunit regulates inactivation of voltage-gated K_ channels. *Biochem Biophys Res Commun.* 2007;359:269-276.

Heiner I, Eisfeld J, Halaszovich CR, Wehage E, Jüngling E, Zitt C Lückhoff A. Expression profile of the transient receptor potential (TRP) family in neutrophil granulocytes: evidence for currents through long TRP channel 2 induced by ADP-ribose and NAD. *Biochem J.* 2003;371: 1045-1053.

Herson PS, Dulock KA, Ashford ML. Characterization of a nicotinamideadenine dinucleotide-dependent cation channel in the CRI-G1 rat insulinoma cell line. *J Physiol.* 1997;505:65-76.

Alvarez J, Camaleno J, Garcia-Sancho J, Herreros B. Modulation of Ca2_-dependent K_transport by modifications of the NAD_/NADH ratio in intact human red cells. *Biochim Biophys Acta.* 1986;856: 408-411.

Zima AV, Copello JA, Blatter LA. Effects of cytosolic NADH/NAD_ levels on sarcoplasmic reticulum Ca2_ release in permeabilized rat ventricular myocytes. *J Physiol.* 2004;555:727-741.

Park MK, Lee SH, Ho WK, Earm YE. Redox agents as a link between hypoxia and the responses of ionic channels in rabbit pulmonary vascular smooth muscle. *Exp Physiol.* 1995;80:835-842.

Aon MA, Cortassa S, Marban E, O'Rourke B. Synchronized whole cell oscillations in mitochondrial metabolism triggered by a local release of reactive oxygen species in cardiac myocytes. *J Biol Chem.* 2003;278: 44735-44744.

Di LF, Menabo R, Canton M, Barile M, Bernardi P. Opening of the mitochondrial permeability transition pore causes depletion of mitochondrial and cytosolic NAD_ and is a causative event in the death of myocytes in postischemic reperfusion of the heart. *J Biol Chem.* 2001; 276:2571-2575.

Choudhary G, Dudley SC Jr. Heart failure, oxidative stress, and ion channel modulation. *Congest Heart Fail.* 2002;8:148-155.

Pillai JB, Isbatan A, Imai Si, Gupta MP. Poly(ADP-ribose) polymerase-1-dependent cardiac myocyte cell death during heart failure is mediated by NAD_ depletion and reduced Sir2_ deacetylase activity. *J Biol Chem.* 2005;280:43121-43130.

Dzhanashiya PK, Vladytskaya OV, Salibegashvili NV. Efficiency and mechanisms of the antioxidant effect of standard therapy and refracterin in the treatment of chronic heart failure in elderly patients with postinfarction cardiosclerosis. *Bull Exp Biol Med.* 2004;138:412-414.

Shang LL, Pfahnl AE, Sanyal S, Jiao Z, Allen J, Banach K, Fahrenbach J, Weiss D, Taylor WR, Zafari AM, Dudley SC Jr. Human heart failure is associated with abnormal C-terminal splicing variants in the cardiac sodium channel. *Circ Res.* 2007;101:1146-1154, and Online Supplement (pp. 1-10).

Makielski JC, Farley A. Na_ current in human ventricle: implications for sodium loading and homeostasis. *J Cardiovasc Electrophysiol.* 2006;17: S15-S20.

Valdivia CR, Chu WW, Pu J, Foell JD, Haworth RA, Wolff MR, Kamp TJ, Makielski JC. Increased late sodium current in myocytes from a canine heart failure model and from failing human heart. *J Mol Cell Cardiol.* 2005;38:475-483.

Ajiro Y, Hagiwara N, Kasanuki H. Assessment of markers for identifying patients at risk for life-threatening arrhythmic events in Brugada syndrome. *J Cardiovasc Electrophysiol.* 2005;16:45-51.

Gellens et al. Primary Structure and Functional Expression of the Human Cardiac Tetrodotoxin-Insensitive Voltage-Dependent Sodium-Channel. *Proceedings of the National Academy of Sciences of the United States of America* 89, 554-558 (1992).

Wang et al. Genomic organization of the human SCN5A gene encoding the cardiac sodium channel. *Genomics* 34, 9-16 (1996).

George et al. Assignment of the human heart tetrodotoxin-resistant voltage-gated Sodium channel alpha-subunit gene (SCN5A) to band 3p21. *Cytogenet. Cell Genet.* 68, 67-70 (1995).

Schott et al. Cardiac conduction defects associate with mutations in SCN5A. *Nat. Genet.* 23, 20-21 (1999).

Tan et al. A calcium sensor in the sodium channel modulates cardiac excitability. *Nature* 415, 442-447 (2002).

Zubay, Biochemistry, Chapter 10, part II Carbohydrate metabolism and chemical energy, p. 400-403 (1984).

Remington's Pharmaceutical Sciences, Mace Publishing Company, Philadelphia, Pa., 17th ed. (1985).

Alings, M. and Wilde A. "Brugada" Syndrome: Clinical Data and Suggested Pathophysiological Mechanism. *Circulation* 1999; 99:666-673.

(56) References Cited

OTHER PUBLICATIONS

Brugada J, Brugada R, Antzelevitch C et al. Long-term follow-up of individuals with the electrocardiographic pattern of right bundle-branch block and ST-segment elevation in precordial leads V1 to V3. *Circulation.* 2002;105:73-78.

Zhou, M. Diwu Z., Panchuk-Voloshina, N. and Haugland. A Stable Nonfluorescent Derivative of Resorufin for the Fluorometric Determination of Trace Hydrogen Peroxide: Applications in Detecting the Activity of Phagocyte NADPH Oxidase and Other Oxidases. Analytical Biochemistry 253 (1997) 162-168.

Mohanty, J.G., Jaffe, J.S., Schulman, E.S. and Raible, D.G.. A Highly Sensitive Fluorescent Micro-Assay of H2O Release from Activated Human Leukocytes Using a Dihydroxyphenoxazine Derivative. Journal of Immunological Methods 202 (1997) 133-141.

Liu M, Sanyal S, Gao G, Gurung IS, Zhu X, Gaconnet G, Kerchner LJ, Shang LL, Huang CLH, Grace A, London B, Dudley SC, Jr. Cardiac $Na^+$ current regulation by pyridine nucleotides. *Circ Res.* 2009; 105:737-45, Supplemental Material (pp. 1-8), and Author manuscript Cir Res Oct. 2009; 105(8):737-745.

Shaw RM, Rudy Y. Ionic mechanisms of propagation in cardiac tissue: roles of the sodium and L-type calcium currents during reduced excitability and decreased gap junction coupling. *Circ Res.* 1997; 81:727-41.

Shimizu W, Aiba T, Kamakura S. Mechanisms of disease: current understanding and future challenges in Brugada syndrome. *Nat Clin Pract Cardiovasc Med.* 2005; 2:408-14.

Andrukhiv A, Costa ADT, West I, Garlid KD. Opening of $mitoK_{ATP}$ increases superoxide generation from complex I of the electron transport chain. *Am J Physiol Heart Circ Physiol.* 2006; 291:H2067-H2074.

Ide T, Tsutsui H, Kinugawa S, Utsumi H, Kang D, Hattori N, Uchida K, Arimura Ki, Egashira K, Takeshita A. Mitochondrial electron transport complex I is a potential source of oxygen free radicals in the failing myocardium. *Circ Res.* 1999; 85:357-63.

Mallat Z, Philip I, Lebret M, Chatel D, Maclouf J, Tedgui A. Elevated levels of 8-iso-prostaglandin F2a in pericardial fluid of patients with heart failure : a potential role for in vivo oxidant stress in ventricular dilatation and progression to heart failure. *Circulation.* 1998: 97:1536-9.

Hill MF, Singal PK. Right and left myocardial antioxidant responses during heart failure subsequent to myocardial infarction. *Circulation.* 1997; 96:2414-20 (11 pages).

Dhalla AK, Singal PK. Antioxidant changes in hypertrophied and failing guinea pig hearts. *Am J Physiol Heart Circ Physiol.* 1994; 266:H1280-H1285.

Brady N, Hamacher-Brady A, Westerhoff H, Gottlieb R. A wave of reactive oxygen species (ROS)-induced ROS release in a sea of excitable mitochondria. *Antioxid Redox Signal.* 2006; 8:1651-65.

Zorov DB, Filburn CR, Klotz LO, Zweier JL, Sollott SJ. Reactive oxygen species (ROS)-induced ROS release: a new phenomenon accompanying induction of the mitochondrial permeability transition in cardiac myocytes. *J Exp Med.* 2000; 192:1001-14.

Costa ADT, Pierre SV, Cohen MV, Downey JM, Garlid KD. cGMP signalling in pre- and post-conditioning: the role of mitochondria. *Cardiovasc Res.* 2008; 77:344-52.

Ogbi M, Chew CS, Pohl J, Stuchlik O, Ogbi S, Johnson JA. Cytochrome c oxidase subunit IV as a marker of protein kinase Ce function in neonatal cardiac myocytes: implications for cytochrome c oxidase activity. *Biochem J.* 2004; 382:923-32.

Clarke SJ, McStay GP, Halestrap AP. Sanglifehrin A Acts as a Potent Inhibitor of the Mitochondrial Permeability Transition and Reperfusion Injury of the Heart by Binding to Cyclophilin-D at a Different Site from Cyclosporin A. *J Biol Chem* 2002;277:34793-9.

Sato T, O'Rourke B, Marban E. Modulation of mitochondrial ATP-dependent $K^+$ channels by protein kinase C. *Circ Res.* 1998; 83:110-4.

O'Rourke B. Evidence for mitochondrial $K^+$ channels and their role in cardioprotection. *Circ Res.* 2004; 94:420-32, and Supplement (pp. 1-6).

Chen Q, Vazquez E, Moghaddas S, Hoppel C, Lesnefsky E. Production of reactive oxygen species by mitochondria. *J Biol Chem.* 2003; 278:36027-31.

Akar FG, Aon MA, Tomaselli GF, O'Rourke B. The mitochondrial origin of postischemic arrhythmias. *J Clin Invest.* 2005; 115:3527-35.

Murphy MP. How mitochondria produce reactive oxygen species. *Biochem J.* 2009; 417:1-13.

O'Rourke B, Ramza B, Marban E. Oscillations of membrane current and excitability driven by metabolic oscillations in heart cells. *Science.* 1994; 265:962-6.

Murray KT, Hu N, Daw JR, Shin HG, Watson MT, Mashburn AB, George AL Jr. Functional effects of protein kinase C activation on the human cardiac Na_ channel. *Circ Res.* 1997;80:370-376.

Zhou J, Yi J, Hu N, George AL Jr, Murray KT. Activation of protein kinase A modulates trafficking of the human cardiac sodium channel in *Xenopus oocytes*. *Circ Res.* 2000;87:33-38.

Hallaq et al. Quantitation of protein kinase A-mediated trafficking of cardiac sodium channels in living cells. Cardiovascular Research 72 (2006) 250-261.

Zhou J, Shin HG, Yi J, Shen W, Williams CP, Murray KT. Phosphorylation and putative ER retention signals are required for protein kinase A-mediated potentiation of cardiac sodium current. *Circ Res.* 2002;91: 540-546.

Zhang F, Jin S, Yi F, Xia M, Dewey WL, Li PL. Local production of O2 by NAD(P)H oxidase in the sarcoplasmic reticulum of coronary arterial myocytes: cADPR-mediated Ca2_ regulation. *Cell Signal.* 2008;20: 637-644.

Nitti et al. PKC signaling in oxidative hepatic damage. Molecular Aspects of Medicine 29 (2008) 36-42.

Bruzzone et al. Extracellular NAD+ regulates intracellular calcium levels and induces activation of human granulocytes. Biochem. J. (2006) 393, 697-704.

Romanello et al. Extracellular NAD1 Induces Calcium Signaling and Apoptosis in Human Osteoblastic Cells. Biochemical and Biophysical Research Communications 285, 1226-1231 (2001).

Budas & Mochly-Rosen. Mitochondrial protein kinase Cε (PKCε): emerging role in cardiac protection from ischaemic damage. Biochemical Society Transactions (2007) vol. 35, part 5, 1052-1054.

Silberman GA, Fan T-H, Liu H, Jiao Z, Xiao HD, Lovelock JD, Boulden B, Widder J, Fredd S, Bernstein KE, Wolska B, Dikalov S, Harrison DG, Dudley SCJr. Uncoupled cardiac nitric oxide synthase mediates diastolic dysfunction. *Circulation.* 2010; 121:519-28, and Supp. Data (21 pp.).

Sorescu D, Weiss D, Lassegue B, Clempus RE, Szocs K, Sorescu GP, Valppu L, Quinn MT, Lambeth JD, Vega JD, Taylor WR, Griendling KK. Superoxide production and expression of Nox family proteins in human atherosclerosis. *Circulation.* 2002; 105:1429-35.

Pacher P, Nivorozhkin A, Szabo C. Therapeutic effects of xanthine oxidase inhibitors: Renaissance half a century after the discovery of allopurinol. *Pharmacol Rev.* 2006; 58:87-114.

Kobayashi K, Neely JR. Control of maximum rates of glycolysis in rat cardiac muscle. *Circ Res.* 1979; 44:166-75.

Li Q, Hwang YC, Ananthakrishnan R, Oates PJ, Guberski D, Ramasamy R. Polyol pathway and modulation of ischemia-reperfusion injury in Type 2 diabetic BBZ rat hearts. *Cardiovasc Diabetol.* 2008; 7:33-44 (11 pages).

Moir AM, Zammit VA. Insulin-independent and extremely rapid switch in the partitioning of hepatic fatty acids from oxidation to esterification in starved-refed diabetic rats. *Biochem J.* 1995; 305:953-8.

van Raam B, Sluiter W, de Wit E, Roos D, Verhoeven A, Kuijpers T. Mitochondrial membrane potential in human neutropils is maintained by complex III activity in the absence of supercomplex organisation. *PLoS ONE.* 2008; 3:e2013 (12 pages).

Liang HL, Arsenault J, Mortensen J, Park F, Johnson CP, Nilakanta V. Partial attenuation of cytotoxicity and apoptosis by SOD1 in ischemic renal epithelial cells. *Apoptosis.* 2009; 14:1176-89.

Dikalova AE, Bikineyeva AT, Budzyn K, Nazarewicz RR, McCann L, Lewis W, Harrison DG, Dikalov SI. Therapeutic targeting of mitochondrial superoxide in hypertension. *Circ Res.* 2010; 107:106-16, and Online Supp. (12 pages).

(56) References Cited

OTHER PUBLICATIONS

Murphy E, Steenbergen C. Preconditioning: the mitochondrial connection. *Annu Rev Physiol.* 2007; 69:51-67.

Barth E, Stämmler G, Speiser B, Schaper J. Ultrastructural quantitation of mitochondria and myofilaments in cardiac muscle from 10 different animal species including man. *J Mol Cell Cardiol.* 1992; 24:669-81.

Boveris A, Oshino N, Chance B. The cellular production of hydrogen peroxide. *Biochem J.* 1972; 128:617-630.

Batandier C, Fontaine E, Keriel C, Leverve X. Determination of mitochondrial reactive oxygen species: methodological aspects. *J Cell Mol Med.* 2002; 6:175-87.

Panov A, Schonfeld P, Dikalov S, Hemendinger R, Bonkovsky HL, Brooks BR. The Neuromediator glutamate, through specific substrate interactions, enhances mitochondrial ATP production and reactive oxygen species generation in monsynaptic brain mitochondria. *J Biol Chem.* 2009; 284:14448-56.

Han D, Antunes F, Canali R, Rettori D, Cadenas E. Voltage-dependent anion channels control the release of the superoxide anion from mitochondria to cytosol. *J Biol Chem.* 2003; 278:5557-63.

Brown D, Aon MA, Akar FG, Liu T, Sorarrain N, O'Rourke B. Effects of 4'-chlorodiazepam on cellular excitation-constraction coupling and ischaemia-reperfusion injury in rabbit heart. *Cardiovasc Res.* 2008; 79:141-9.

Valdivia CR, Ueda K, Ackerman MJ, Makielski JC. GPD1L links redox state to cardiac excitability by PKC-dependent phosphorylation of the sodium channel SCN5A. *AJP—Heart and Circulatory Physiology.* 2009; 297:H1446-H1452.

Zelent B, Troxler T, Vanderkooi JM. Temperature dependence for fluorescence of β-NADH in glycerol/water solution and in trehalose/sucrose glass. *Journal of Fluorescence.* 2007; 17:37-42.

Liu M, Gaconnet G, London B, Dudley, Jr. S.C. A Central Role of Mitochondria in the Regulation of Sodium Current. Presentation at the Cardiac Electrophysiology Society, Orlando, Florida (Nov. 14, 2009) (1 page).

Yang H, Yang T, Baur JA, Perez E, Matsui T, Carmona JJ, Lamming D, Souza-Pinto NC, Bohr VA, Rosenzweig A, de Cabo R, Sauve A, Sinclair DA. Nutrient-sensitive mitochondrial NAD_ levels dictate cell survival. *Cell.* 2007;130:1095-1107.

Lin SJ, Guarente L. Nicotinamide adenine dinucleotide, a metabolic regulator of transcription, longevity and disease. *Curr Opin Cell Biol.* 2003;15:241-246.

Herbert JM, Augereau JM, Gleye J, Maffrand JP. Chelerythrine is a potent and specific inhibitor of protein kinase C. *Biochem Biophys ResCommun.* 1990;172:993-999.

Chao MD, Chen IS, Cheng JT. Inhibition of protein kinase C translocation from cytosol to membrane by chelerythrine. *Planta Med.* 1998;64: 662-663.

Frohnwieser B, Chen L, Schreibmayer W, Kallen R. Modulation of the human cardiac sodium channel alpha-subunit by cAMP-dependent protein kinase and the responsible sequence domain. *J Physiol (London).* 1997;498:309-318.

Glass DB, Lundquist LJ, Katz BM, Walsh DA. Protein kinase inhibitor-(6-22)-amide peptide analogs with standard and nonstandard amino acid substitutions for phenylalanine 10. Inhibition of cAMP-dependent protein kinase. *J Biol Chem.* 1989;264:14579-14584.

Shin HG, Murray KT. Conventional protein kinase C isoforms and cross-activation of protein kinase A regulate cardiac Na_ current. *FEBS Lett.* 2001;495:154-158.

Biswas S, DiSilvestre D, Tian Y, Halperin VL, Tomaselli GF. Calciummediated dual-mode regulation of cardiac sodium channel gating. *Circ Res.* 2009;104:870-878, and Supp. Material (10 pages).

Casini S, Verkerk AO, van Borren MM, van Ginneken AC, Veldkamp MW, de Bakker JM, Tan HL. Intracellular calcium modulation of voltage-gated sodium channels in ventricular myocytes. *Cardiovasc Res.* 2009;81:72-81.

Brisson D, Vohl M, St Pierre J, Hudson T, Gaudet D. Glycerol: a neglected variable in metabolic process? *Bioessays.* 2001;23.6:534-542.

Antzelevitch C, Brugada P, Borggrefe M, et al. Brugada syndrome: report of the second consensus conference: endorsed by the Heart Rhythm Society and the European Heart Rhythm Association. *Circulation.* 2005; 111 :659-670.

Brugada J, Brugada P. Further characterization of the syndrome of right bundle branch block, ST segment elevation, and sudden cardiac death. *J Cardiovasc Electrophysiol.* 1997; 8:325-331.

Grant AD. Electrophysiological basis and genetics of Brugada syndrome. *J Cardiovasc Electrophysiol.* 2005; 16:S3-7.

Chen Q, Kirsch GE, Zhang 0, et al. Genetic basis and molecular mechanism for idiopathic ventricular fibrillation. *Nature.* 1998; 392:293-296.

Priori SG, Napolitano C, Gasparini M, et al. Clinical and genetic heterogeneity of right bundle branch block and ST -segment elevation syndrome: A prospective evaluation of 52 families. *Circulation.* 2000; 102:2509-2515.

Valdivia CR, Tester OJ, Rok BA, et al. A trafficking defective, Brugada syndromecausing SCNSA mutation rescued by drugs. *Cardiovasc Res.* 2004; 62:53-62.

Brugada R, Brugada J, Antzeievitch G, et al. Sodium channel blockers identify risk for sudden death in patients with ST-segment elevation and right bundle branch block but structurally normal hearts. *Circulation.* 2000; 101:510-515.

Pollevick GO, Schimpf R, AizawaY, et al. Loss of function in calcium channel activity secondary to a mutation in CACNB2b modulates the clinical manifestation of a combined Brugada syndrome-hort aT phenotype. *Circulation.* 2006; 114:11-193 (Abstract—3 pages).

Yan GX, Antzelevitch C. Cellular basis for the Brugada syndrome and other mechanisms of arrhythmogenesis associated with ST-segment elevation. *Circulation.* 1999; 100:1660-1666.

Weiss R, Barmada MM, Nguyen T, et al. Clinical and molecular heterogeneity in the Brugada syndrome: a novel gene locus on chromosome 3. *Circulation.* 2002;105:707-713.

Walz AG, Demel RA, de Kruijff S, et al. Aerobic sn-glycerol-3-phosphate dehydrogenase from *Escherichia coli* binds to the cytoplasmic membrane through an amphipathic alpha-helix. *Biochem J.* 2002; 365:471-479.

Myerburg RJ, Castellanos A. Cardiac arrest and sudden cardiac death. In: P. ZD, Libby P, Bonow RO, et al., eds. Braumwald's Heart disease: A *textbook of cardiovascular medicine.* 7th ed. Phildadelphia: Elsevier Saunders; 2005:865-908 (Chapter 33).

Priori SG, Rivolta I, Napolitano C. Genetics of long QT, Brugada, and other channelopathies. In: P. ZD, Jalife J, eds. *Cardiac Electrophysiology. From Cell to Bedside.* 4th ed. Philadelphia: Saunders; 2004:462-470 (Chapter 50).

Sarkozy A, Brugada P. Sudden Cardiac Death and Inherited Arrhythmia Syndromes. *J Cardiovasc Electrophysiol.* 2005; 16:S8-20.

Mohler PJ, Schott JJ, Gramolini AO, et al. Ankyrin-B mutation causes type 4 long-QT cardiac arrhythmia and sudden cardiac death. *Nature.* 2003; 21:634-639.

Corrado 0, Thiene G. Arrhythmogenic right ventricular cardiomyopathy/dysplasia: clinical impact of molecular genetic studies. *Circulation.* 2006; 113:1634-1637.

Schwartz PJ, Priori SG, Dumaine R, et al. A molecular link between the sudden infant death syndrome and the long-QT syndrome. *N Engl J Med.* 2000;343:262-267.

Van Norstrand OW, Valdivia CR, Tester OJ, et al. Molecular and functional characterization of a novel GPD1-L mutations in sudden Infant Death Syndrome. Circulation 2007; 116-2253-2259.

Royer A, van Veen TA, Le Bouter S, et al. Mouse model of SCNSA-linked hereditary Lenegre's disease: age-related conduction slowing and myocardial fibrosis. *Circulation.* 2005; 111: 1738-1746.

Tan HL, Bink-Boelkens MT, Bezzina CR, et al. A sodium-channel mutation causes isolated cardiac conduction disease. *Nature.* 2001; 409:1043-1047.

Mihm MJ, Yu F, Cames CA, et al. Impaired myofibrillar energetics and oxidative injury during human atrial fibrillation. *Circulation.* 2001; 104:174-180.

Fukuda K, Davies SS, Nakajima T, et al. Oxidative mediated lipid peroxidation recapitulates proarrhythmic effects on cardiac sodium channels. *Circ Res.* 2005; 97:1262-1269.

(56) References Cited

OTHER PUBLICATIONS

Rubart M, Zipes DP. Mechanisms of sudden cardiac death. *J Clin Invest.* 200S; 115:2305-2315.
CAST. Preliminary report: effect of encainide and flecainide on mortality in a randomized trial of arrhythmia suppression after myocardial infarction. The Cardiac Arrhythmia Suppression Trial (CAST) Investigators. *N Engl J Med.* 1989; 321:406-412.
PCT International Search Report and Written Opinion dated Jan. 30, 2009, in International App. No. PCT/US2008/011919 (12 pp.).
Krebs et al. (1999). "Na+ translocation by the NADH:ubiquinone oxidoreductase (complex I) from *Klebsiella pneumoniae*." Molecular Microbiology 33(2):590-598.
Udagawa et al. (1986). "Generation of Na+ electrochemical potential by the Na+-motive NADH oxidase and Na+/H+ antiport system of a moderately halophilic Vibrio costicola." J. Biol. Chem. 261(6):2616-2622.
Sanyal et al. Circulation, Oct. 16, 2007. 116(16) S185-S186, Abstract 941.
Office Action (Restriction Requirement) dated Jul. 6, 2010, in U.S. Appl. No. 12/289,005, filed Oct. 17, 2008.
Office Action dated Oct. 5, 2010, in U.S. Appl. No. 12/289,005, filed Oct. 17, 2008.
Notice of Allowance dated Jun. 23, 2011, in U.S. Appl. No. 12/289,005, filed Oct. 17, 2008.
Office Action dated Oct. 3, 2011, in co-pending U.S. Appl. No. 13/067,953, filed Jul. 11, 2011.
U.S. Appl. No. 13/067,953, filed Jul. 11, 2011.
U.S. Appl. No. 13/091,972, filed Apr. 21, 2011.
U.S. Appl. No. 11/895,883, filed Aug. 27, 2007.
U.S. Appl. No. 13/507,319, filed Jun. 21, 2012.
U.S. Appl. No. 13/551,790, filed Jul. 18, 2012.
U.S. Appl. No. 13/585,396, filed Aug. 14, 2012.
U.S. Appl. No. 11/707,882, filed Feb. 20, 2007.
U.S. Appl. No. 13/658,943, filed Oct. 24, 2012.
Office Action dated Oct. 12, 2012, in U.S. Appl. No. 13/091,972, filed Apr. 21, 2011.
Ouzounian et al. Diastolic heart failure: mechanisms and controversies. Nature Clinical Practice Cardiovascular Medicine. 5(7):375-386, Jul. 2008.
Reed et al. FASEB Journal. The senescence-accelerated mouse: a model for the investigation of age-related oxidative stress and diastolic dysfunction. 22:Meeting Abstract Supplement, Mar. 2008, 970.39 (2 pages).
Li et al. Aging induces cardiac diastolic dysfunction, oxidative stress, accumulation of advanced glycation endproducts and protein modification. Aging Cell. 4(2):57-64, Apr. 2005.
Westermann et al. Cardiac Inflammation Contributes to Changes in the Extracellular Matrix in Patients with Heart Failure and Normal Ejection Fraction. Circulation Heart Failure. 2011;4:44-52.
Satpathy et al. Diagnosis and management of diastolic dysfunction and heart failure. American Family Physician. 73(5):841-846. Mar. 1, 2006.
Kuwahara et al. Transforming Growth Factor-β Function Blocking Prevents Myocardial Fibrosis and Diastolic Dysfunction in Pressure-Overloaded Rats. Circulation; 106:130-135, 2002.
Leask, Andrew. TGF-β, cardiac fibroblasts, and the fibrotic response. Cardiovascular Research. 74:207-212, Jul. 21, 2006.
Reed et al. Diastolic Dysfuntion is Associated with Cardiac Fibrosis in the Senecence-Accelerated Mouse. Circulation 120(18), Supplement 2, S762-5763, Nov. 3, 2009 (1 page).
Blom et al. Gene regulation of connective tissue growth factor: new targets for antifibrotic therapy? Matrix Biology 21 (2002) 473-482.
Kleber AG. Mechanism of Ventricular Arrhythmias: A Perspective. J. Cardiovascular Pharmacology 17(Suppl. 6):S1-S8, 1991.
Salama G et al. Deciphering Arrhythmia Mechanisms—Tools of the Trade. Card Electrophysiol Clin. Mar. 2011; 3(1):11-21 (15 pages).
Moens AL et al. Myocardial ischemia/reperfuion-injury, a clinical view on a complex pathophysiological process. International Journal of Cardiology 100 (2005) 179-190.
Li et al. Targeting mitochondrial reactive oxygen species as novel therapy for inflammatory diseases and cancers, Journal of Hematology & Oncology 2013, 6:19 (19 pgs).
Smith et al. Mitochondrial pharmacology, Trends in Pharmacological Sciences, Jun. 2012, vol. 33, No. 6, 341-352.
Sovari et al. Mitochondria Oxidative Stress, Connexin43 Remodeling, and Sudden Arrhythmic Death, *Circ Arrhythm Electrophysiol.* 2013;6:623-631.
Liu M, Liu H, Dudley SC, Jr. Reactive oxygen species originating from mitochondria regulate the cardiac sodium channel. *Circ Res.* 2010;107:967-74, with supplement (5 pgs).
Sovari AA, Rutledge CA, Jeong E-M, Dolmatova E, Arasu D, Liu H, Vandani N, Gu L, Zandieh S, Xiao L, Bonini MG, Duffy HS, Dudley SC. Mitochondria-Targeted Antioxidant Therapy Prevents Connexin 43 Remodeling and Sudden Death Caused by Renin-Angiotensin System Activation. Circulation. 2012; 126: A19711 (3 pages).
Sovari AA, Jeong EM, Zandieh S, Gu L, Iravanian S, Bonini M, Dudley SC. Mitochondria-Targeted Antioxidant Therapy Prevents Angiotensin II Medicated Connexin 43 Remodeling and Sudden Arrhythmic Death. Circulation, vol. 124, (21 Meeting Abs.) Supp. 1, Nov. 22, 2011. Abstract 15801 (1 pg).
Office Action dated Sep. 6, 2013, in U.S. Appl. No. 13/507,319, filed Jun. 21, 2012.
Office Action dated Sep. 6, 2013, in U.S. Appl. No. 13/551,790, filed Jul. 18, 2012.
Office Action dated Sep. 6, 2013, in U.S. Appl. No. 13/585,396, filed Aug. 14, 2012.
Li et al. Mitchondrial dysfunction causing cardiac sodium channel downregulation in cardiomyopathy. *Journal of Molecular and Cellular Cardiology* 54 (2013) 25-34.
Sovari et al. (2013). Mitochondria Oxidative Stress, Connexin43 Remodeling, and Sudden Arrhythmic Death, *Circ Arrhythm Electrophysiol.* 2013;6:623-631 (with Supplemental Material (7 pgs.). Orig. published online Apr. 4, 2013.
Lotrionte et al. Review and Meta-Analysis of Incidence and Clinical Predictors of Anthracycline Cardiotoxicity. *Am J Cardiol* 2013;112:1980-1984.
Mackay et al. Assessment of Anthracycline Cardiomyopathy by Endomycardial Biopsy. Ultrastructural Pathology, 18:203-211, 1994.
Chatterjee et al. Doxorubicin Cardiomyopathy. *Cardiology* 2010;115:155-162.
Angelis et al. Anthracycline Cardiomyopathy Is Mediated by Depletion of the Cardiac Stem Cell Pool and Is Rescued by Restoration of Progenitor Cell Function. *Circulation.* 2010;121:276-292.
Mazevet et al. Complications of chemotherapy, a basic science update. *Presse Med.* 2013; 42; e352-e361.
Octavia et al. Doxorubicin-induced cardiomyopathy: From molecular mechanisms to therapeutic strategies. *Journal of Molecular and Cellular Cardiology* 52 (2012) 1213-1225.
Chanan-Khan et al. Prevention and Management of Cardiotoxicity From Antineoplastic Therapy. *J Support Oncol.* 2004; 2:251-266.
Office Action dated Nov. 5, 2013, in U.S. Appl. No. 13/507,319, filed Jun. 21, 2012.
Office Action dated Nov. 6, 2013, in U.S. Appl. No. 13/551,790, filed Jul. 18, 2012.
Office Action dated Nov. 6, 2013, in U.S. Appl. No. 13/585,396, filed Aug. 14, 2012.
Sovari et al. Mitochondria-targeted antioxidant, Mito-TEMPO, prevents angiotensin II medicated connexin 43 remodeling and sudden cardiac death. Journal of Investigative Medicine (Apr. 2011) vol. 59, No. 4, pp. 693-694, Abstract No. 6. Meeting Info: 2011 Combined Annual Meeting of the American Federation for Medical Research, Chicago, IL, US. Apr. 14, 2011-Apr. 15, 2011.
Iravanian et al. Heart Rhythm 2008, 5(6 Supplement): s12-s17.
Tomaselli et al. Oxidative Stress Irritates the Heart. Nature Medicine 2010, vol. 16, No. 6, 648-649.
Murphy et al. Targeting Antioxidants to Mitochondria by Conjugation to Lipophilic Cations. Annu. Rev. Pharmacol. Toxicol. 2007 47:629-656.
Alexis Biochemicals Catalog pp. 1-48, published Apr. 2007.
U.S. Appl. No. 14/083,841, filed Nov. 19, 2013.

(56) References Cited

OTHER PUBLICATIONS

Office Action dated Jul. 28, 2014, in U.S. Appl. No. 13/507,319, filed Jun. 21, 2012.
Office Action dated Jun. 25, 2014, in U.S. Appl. No. 13/551,790, filed Jul. 18, 2012.
Office Action dated Jun. 17, 2014, in U.S. Appl. No. 13/585,396, filed Aug. 14, 2012.
Davies et al. Redox Cycling of Anthracyclines by Cardiac Mitochondria, 1986, *The Journal of Biological Chemistry*, vol. 261, No. 7, 3068-3074.
Felker et al., Underlying Causs and Long-Term Survival in Patients with Initially Unexplained Cardiomyopathy. *The New England Journal of Medicine*, 2000, vol. 342, No. 15, 1077-84.
Octavia Y. et al., Doxorubicin-induced cardiomyopathy: From molecular mechanisms to therapeutic strategies. *Journal of Molecular and Cellular Cardiology*, 52, 2012, 1213-1225.
Guilherme H. et al., Increased Need for Right Ventricular Support in Patients With Chemotherapy-Induced Cardiomyopathy Undergoing Mechanical Circulatory Support. *Journal of the American College of Cardiology*, 2014, vol. 63, No. 3, 240-248.
Tabane K. et al. Cancer drugs: Highlighting the molecular mechanisms of cardiotoxicity. SA Heart, 2012;9:244-248.
Zhang S. et al., Identification of the molecular basis of doxorubicin-induced cardiotoxicity. *Nature Medicine*, 2012, vol. 18, No. 11, 1639-1642. With Online Methods (3 pgs).
Ichikawa I. et al., Cardiotoxicity of doxorubicin is mediated through mitochondrial iron accumulation. *Journal of Clinical Investigation*, 2014; vol. 124, No. 2:617-630.
Jeyaseelan R. et al., A novel Cardiac-Restricted Target for Doxorubicin. *The Journal of Biological Chemistry*, 1997, vol. 272, No. 36, 22800-22808.
International Classification of Diseases (ICD) http://www.who.int/classifications/icd/en/ (2 pages) Accessed Jul. 16, 2014.
Cardiomyopathy (I42) and cardiomyopathy due to drug or external agent (I42.7) http://apps.who.int/classifications/icd10/browse/2010/en#/I30-I52 (1 page) Accessed Jul. 16, 2014.
Epstein AE, DiMarco JP, Ellenbogen KA, Estes NA, III, Freedman RA, Gettes LS, Gillinov AM, Gregoratos G, Hammill SC, Hayes DL, Hlatky MA, Newby LK, Page RL, Schoenfeld MH, Silka MJ, Stevenson LW, Sweeney MO, Tracy CM, Epstein AE, Darbar D, DiMarco JP, Dunbar SB, Estes NA, III, Ferguson TB, Jr., Hammill SC, Karasik PE, Link MS, Marine JE, Schoenfeld MH, Shanker AJ, Silka MJ, Stevenson LW, Stevenson WG, Varosy PD. 2012 ACCF/AHA/HRS focused update incorporated into the ACCF/AHA/HRS 2008 guidelines for device-based therapy of cardiac rhythm abnormalities: a report of the American College of Cardiology Foundation/American Heart Association Task Force on Practice Guidelines and the Heart Rhythm Society. *J Am Coll Cardiol* 2013;61:e6-75.
Nakahara S, Tung R, Ramirez RJ, Michowitz Y, Vaseghi M, Buch E, Gima J, Wiener I, Mahajan A, Boyle NG, Shivkumar K. Characterization of the arrhythmogenic substrate in ischemic and nonischemic cardiomyopathy implications for catheter ablation of hemodynamically unstable ventricular tachycardia. *J Am Coll Cardiol* 2010;55:2355-65.
Boriani G, Gasparini M, Lunati M, Santini M, Landolina M, Vincenti A, Curnis A, Bocchiardo M, Padeletti L, Biffi M, Allaria L, Denaro A. Characteristics of ventricular tachyarrhythmias occurring in ischemic versus nonischemic patients implanted with a biventricular cardioverter-defibrillator for primary or secondary prevention of sudden death. *Am Heart J* 2006;152:527-11.
Lindsay BD, Ambos HD, Schechtman KB, Arthur RM, Cain ME. Noninvasive detection of patients with ischemic and nonischemic heart disease prone to ventricular fibrillation. *J Am Coll Cardiol* 1990;16:1656-64.
Rouleau J, Shenasa M, de CJ, Nadeau R. Predictors of survival and sudden death in patients with stable severe congestive heart failure due to ischemic and nonischemic causes: a prospective long term study of 200 patients. *Can J Cardiol* 1990;6:453-60.
Ehlert FA, Cannom DS, Renfroe EG, Greene HL, Ledingham R, Mitchell LB, Anderson JL, Halperin BD, Herre JM, Luceri RM, Marinchak RA, Steinberg JS. Comparison of dilated cardiomyopathy and coronary artery disease in patients with life-threatening ventricular arrhythmias: Differences in presentation and outcome in the AVID registry. *Am Heart J* 2001;142:816-22.
Contractor T, Beri A, Gardiner J, Ardhanari S, Thakur R. Statins reduce appropriate implantable cardioverter-defibrillator shocks in ischemic cardiomyopathy with no benefit in nonischemic cardiomyopathy. *Am J Ther* 2012;19:413-8.
Furushima H, Chinushi M, Okamura K, Komura S, Tanabe Y, Sato A, Izumi D, Aizawa Y. Effect of dl-sotalol on mortality and recurrence of ventricular tachyarrhythmias: ischemic compared to nonischemic cardiomyopathy. *Pacing Clin Electrophysiol* 2007;30:1136-41.
Latif S, Dixit S, Callans DJ. Ventricular arrhythmias in normal hearts. *Cardiol Clin* 2008;26:367-80, vi.
Sadek MM, Marchlinski FE. Ablation of ventricular arrhythmias. *Trends Cardiovasc Med* 2014;24:296-304.
Hoffmayer KS, Gerstenfeld EP. Diagnosis and management of idiopathic ventricular tachycardia. *Curr Probl Cardiol* 2013;38:131-58.
Roberts-Thomson KC, Lau DH, Sanders P. The diagnosis and management of ventricular arrhythmias. *Nat Rev Cardiol* 2011;8:311-21.
Morin DP, Lerman BB. Management of ventricular tachycardia in the absence of structural heart disease. *Curr Treat Options Cardiovasc Med* 2007;9:356-63.
Liu M, Liu H, Jeong EM, Gu L, Dudley SC. Mitochondrial reactive oxygen species regulate the cardiac $Na^+$ channel in heart failure. *Basic Cardiovascular Sciences 2011 Scientific Sessions* 2011;Abstract:2011-A-246-AHA-BCVS.
Rutledge CA, Ng FS, Sulkin MS, Greener ID, Sergeyenko AM, Liu H, Gemel J, Beyer EC, Sovari AA, Efimov IR, Dudley SC. c-Src kinase inhibition reduces arrhythmia inducibility and connexin43 dysregulation after myocardial infarction. *J Am Coll Cardiol* 2014;63:928-34.

* cited by examiner

METHOD FOR MODULATING OR CONTROLLING SODIUM CHANNEL CURRENT BY REACTIVE OXYGEN SPECIES (ROS) ORIGINATING FROM MITOCHONDRIA

CROSS-REFERENCE TO RELATED APPLICATIONS

This is a continuation-in-part (CIP) application of U.S. application Ser. No. 12/289,005, filed Oct. 17, 2008, which claims the priority benefit of U.S. Provisional Patent Application Ser. No. 60/960,883, filed Oct. 18, 2007, both of which are hereby incorporated herein in their entirety by reference. This application further claims the priority benefit of U.S. Provisional Patent Application Ser. No. 61/305,668, filed Feb. 18, 2010, which is also hereby incorporated herein in its entirety by reference.

STATEMENT REGARDING FEDERALLY SPONSORED RESEARCH OR DEVELOPMENT

The invention was made with government supported under grants R01 HL085558, R01 HL073753, and P01 HL058000 awarded by the NIH. The government has certain rights in the invention.

FIELD AND BACKGROUND OF THE INVENTION

The present invention is generally directed to regulating sodium channels in a cell, and more particularly to a method for modulating sodium channel current in a cell by reactive oxygen species (ROS) originating from mitochondria.

Recently, we reported that mutations in glycerol-3-phosphate dehydrogenase 1-like (GPD1-L) protein, a gene associated with Brugada Syndrome and Sudden Infant Death Syndromes (References 1 and 2), cause reduced cardiac sodium channel ($Na_v1.5$) function by modulating pyridine nucleotides (Reference 3). Elevated intracellular NADH results in a rapid decrease in cardiac $Na^+$ current ($I_{Na}$) in cardiomyocytes that is large enough to be clinically significant (Reference 4) and of a magnitude seen in Brugada Syndrome (Reference 5). The effect is identical on heterologously expressed sodium channel in human embryonic kidney (HEK) cells. The immediacy of the NADH effect on reducing $I_{Na}$ and the lack of change in mRNA abundance under various experimental conditions suggests that the effect of NADH is post-transcriptional.

NADH modulated $Na_v1.5$ through PKC activation and increased oxidative stress (Reference 3). The finding that the balance of oxidized and reduced NAD(H) regulates $I_{Na}$ suggests that the metabolic state of myocytes may influence $Na_v1.5$. NADH is known to oscillate with myocardial ischemia, and mitochondrial injury is associated with increased NADH and ROS levels (References 6 and 7). These changes in NADH could contribute to reduced $I_{Na}$, conduction block, and arrhythmic risk known to exist with ischemia. Moreover, heart failure is associated with increased oxidative stress, reduced $NAD^+$, and increased NADH (References 8-10). The increased NADH level may contribute to the increased oxidative stress and diminished $I_{Na}$ in heart failure (References 11 and 12).

Several metabolic pathways are known to produce ROS, including uncoupled nitric oxide synthase (NOS), the NAD(P)H oxidase, xanthine oxidase, and the mitochondrial electron transport chain (ETC). Cardiac oxidation leads to NOS uncoupling and diastolic dysfunction (Reference 13). NAD(P)H oxidases are an important source of superoxide in human atherosclerosis (Reference 14). Xanthine oxidase plays an important role in various forms of ischemic injury and in chronic heart failure (Reference 15). In ischemia/reperfusion injury, the ETC serves as the source of ROS (Reference 16). In chronic heart failure, ROS levels increase (References 17 and 18) and myocardial antioxidant reserve decreases (References 19 and 20). In turn, ROS increases cell death by apoptosis, reduces cellular respiration, induces structural damage to proteins including ion channels, and impairs contractility (Reference 8).

Aspects of the Invention

The present disclosure is directed to various aspects of the present invention.

One aspect of the present invention includes discovery and/or demonstration that mitochondria are the main source of NADH-dependent ROS downregulating sodium channel current ($I_{Na}$) in cardiac cells.

Another aspect of the present invention includes discovery and/or demonstration that mitochondrial superoxide release is responsible for downregulation of $I_{Na}$.

Another aspect of the present invention includes discovery and/or demonstration that elevation in intracellular NADH results in activation of protein kinase C (PKE) and subsequent mitochondrial complex III release of reactive oxygen species (ROS) through the mitochondrial inner member anion channel (IMAC).

Another aspect of the present invention includes discovery and/or demonstration that inhibition of mitochondrial ROS overproduction by one or more strategies prevents or suppresses $I_{Na}$ downregulation by NADH.

Another aspect of the present invention includes suggestions and/or development of possible therapeutic approaches or strategies to reduce or prevent arrhythmic risk generally associated with cardiomyopathy.

Another aspect of the present invention includes a method of modulating or controlling sodium channel current of a cell by activating or inducing mitochondrial reactive oxygen species (ROS) production in the cell.

Another aspect of the present invention includes a method of reducing arrhythmic risk by administering a mitochondrial targeted antioxidant to an individual.

BRIEF DESCRIPTION OF THE DRAWINGS

One of the above and other aspects, novel features and advantages of the present invention will become apparent from the following detailed description of the non-limiting preferred embodiment(s) of invention, illustrated in the accompanying drawings, wherein.

DETAILED DESCRIPTION OF THE PREFERRED EMBODIMENT(S) OF THE INVENTION

Figure 1:
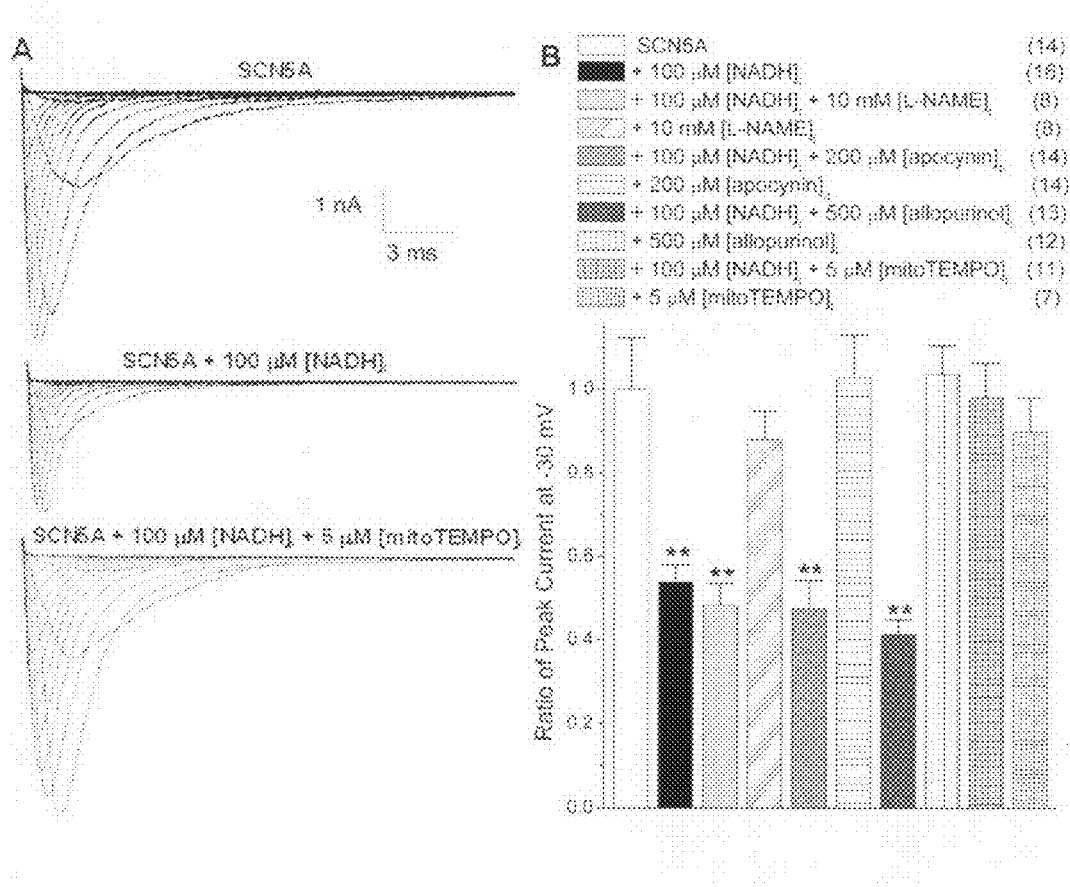
FIG. 1 illustrates that the source of ROS induced by NADH is the mitochondria. (A) Representative traces of $I_{Na}$ demonstrate the decrease in current in the presence of $[NADH]_i$ (100 µmol/L) was blocked by mitoTEMPO (5 µmol/L). (B) The downregulation of peak $I_{Na}$ by $[NADH]_i$ at 100 µmol/L (**P<0.01 versus SCN5A group) is not reversed by L-NAME, apocynin, or allopurinol (P>0.05 versus NADH group), but is reversed by mitoTEMPO at 5 µmol/L (P>0.05 versus SCN5A group, P<0.01 versus NADH group). All these compounds have no effect on $I_{Na}$ when applied alone (P>0.05 versus SCN5A group). Numbers in parentheses indicate the number of experiments.

The present invention is based, at least in part, on the discovery and/or demonstration that mitochondria are the main source of NADH-dependent ROS downregulating the cardiac $Na_v1.5$.

Altered cardiac metabolism is associated with increased risk of arrhythmias and sudden death. In part, this occurs because of reduced electrical conduction in the cardiomyocytes, but the mechanisms for this are not clear. As noted above, we have shown previously that a mutation in GPD1-L protein, causing the sudden death condition Brugada syndrome, reduces $I_{Na}$ by raising intracellular NADH levels and inducing ROS. Here, we investigated the source of ROS induced by elevated NADH. We found that elevated NADH induced ROS production from mitochondria and that ROS released from the mitochondria was mediated by the IMAC. $NAD^+$, inhibition of mitochondrial electron transport, a mitochondrial targeted antioxidant, and an IMAC modulator could prevent the reduction in $I_{Na}$ by reducing mitochondrial ROS production. These findings contribute to our understanding of the mechanisms of conduction block and arrhythmia when cardiac metabolism is disordered. In addition, they suggest possible therapeutic strategies to reduce arrhythmic risk associated with cardiomyopathy.

Methods

All chemicals were purchased from Sigma (St. Louis, Mo.) except: diazoxide and FGIN-1-27 (Enzo Life Sciences International, Inc., Plymouth Meeting, Pa.); chelerythrine and cyclosporin A (Alomone Labs, Jerusalem, Israel); and Hoechst 33342, MitoSOX™ Red, and tetramethylrhodamine methyl ester (TMRM) (Molecular Probes, Eugene, Oreg.). MitoTEMPO was a generous gift from Dr. Sergey Dikalov (Emory University, Atlanta, Ga.).

Cell Culture

We maintained a human embryonic kidney (HEK) cell line stably expressing the human cardiac $Na_v1.5$ channel (SCN5A cells). Expression of $Na_v1.5$ was linked to green fluorescent protein (GFP) expression by an internal ribosomal entry site (SCN5A-IRES-GFP). SCN5A cells were cultured in Dulbecco's modified Eagle's medium with 10% fetal calf serum, 0.2 mg/mL geneticin (for antibiotic selection) and 1% penicillin/streptomycin in a 95% $O_2$/5% $CO_2$ incubator at 37° C. Rat neonatal ventricular myocytes (NVM) were isolated from neonatal rat hearts by collagenase treatment (Worthington Biochemical Corporation, Lakewook, N.J.).

Nearly undetectable levels of GPD1-L protein are expressed in HEK cells (Reference 1). Therefore, for whole-cell patch clamping experiments to study GPD1-L effects on $Na_v1.5$, SCN5A cells were transiently transfected with WT or A280V GPD1-L (a generous gift from Dr. Barry London, University of Pittsburgh, Pa.) and an expression vector containing red fluorescent protein (RFP) as described previously (Reference 2). In these experiments, cells expressing both GFP and RFP were studied.

Electrophysiology $Na^+$ currents were measured using the whole-cell patch clamp technique in voltage-clamp mode at room temperature. Pipettes (1-2 MΩ) were filled with a pipette solution containing (in mmol/L): CsCl 80, cesium aspartate 80, EGTA 11, $MgCl_2$ 1, $CaCl_2$ 1, HEPES 10, and $Na_2ATP$ 5 (adjusted to pH 7.4 with CsOH). The bath solution consisted of (in mmol/L): NaCl 130, CsCl 5, $CaCl_2$ 2, $MgCl_2$ 1.2, HEPES 10 and glucose 5 (adjusted to pH 7.4 with CsOH). A stepped voltage protocol from −100 to +60 mV with a holding potential of −100 mV was applied to establish the presence of voltage-gated $Na_v1.5$ channels. Peak currents obtained during steps to −20 or −30 mV were used for comparison in determining the relative reduction of $I_{Na}$. Steady state fast inactivation was assessed during voltage depolarization from a holding potential of −140 to −20 mV for 500 ms, and measuring current at −20 mV. In all recordings, 80% of the series resistance was compensated, yielding a maximum voltage error of ~1 mV. Data were sampled at 50 kHz and later low pass filtered at 10 kHz for analysis. Currents were recorded and analyzed with an Axopatch 200B amplifier, Axon Digidata 1320A A/D converter and pClamp software (Molecular Devices, Sunnyvale, Calif.). To minimize time-dependent drift in gating parameters, all protocols were initiated 2-5 min after whole-cell configuration was obtained. The currents were normalized with cell capacitance prior to deriving ratios.

Rat NVM action potentials were measured using the whole-cell patch clamp technique in current-clamp mode at room temperature. Pipettes (2-4 MΩ) were filled with a pipette solution containing (in mmol/L): NaCl 10, potassium glutamate 130, EGTA 1.0, $MgCl_2$ 0.5, KCl 9, HEPES 10, glucose 10, and MgATP 5 (adjusted to pH 7.4 with KOH). The bath solution consisted of (in mmol/L): NaCl 140, KCl 5, $CaCl_2$ 2, $MgCl_2$ 1.0, HEPES 10 and glucose 10 (adjusted to pH 7.4 with NaOH). Action potentials were evoked by brief (4 ms) current injections applied at 0.8-1 Hz. Eighty percent of the series resistance was compensated, yielding a maximum voltage error of ~1 mV. Data were sampled at 50 kHz and later low pass filtered at 10 kHz for analysis. Action potentials were recorded and analyzed with an Axopatch 200B amplifier, Axon Digidata 1320A A/D converter and pClamp software.

The following specific inhibitors or activators were applied directly in the pipette solution, alone or together: NADH (100-500 μmol/L), $N^{\omega}$-nitro-L-arginine methyl ester (L-NAME, 1-20 mmol/L), allopurinol (200 μmol/L), mitoTEMPO (5-20 μmol/L), rotenone (1-5 μmol/L), antimycin A (20-40 μmol/L), azide (10 mmol/L), 5-hydroxydecanoate (5-HD, 300 μmol/L), 4,4'-diisothiocyanatostilbene-2,2'-disulfonic acid (DIDS, 500 μmol/L), cycloporine A (CsA, 0.5 μmol/L), PK11195 (50 μmol/L), 4'-chlorodiazepam (4'-CD, 40-100 μmol/L), and FGIN-1-27 (500 μmol/L). Apocynin (100-300 μmol/L), forskolin (1-5 μmol/L), NAD (500 μmol/L) and malonate (1 mmol/L) were applied to bath solution, respectively. Concentrations were determined in our laboratory or by using the similar values used in literatures.

Intracellular NADH Level

Intracellular NADH levels ($[NADH]_i$) were detected by using the EnzyChrom™ $NAD^+$/NADH Assay Kit (BioAssay Systems, Hayward, Calif.) in SCN5A cells with or without treatment of 1 mmol/L pyruvate and 10 mmol/L lactate for 10 min at room temperature. The intensity difference of the reduced product color, measured at 565 nm at time zero and 15 min later, was proportional to the change in $[NADH]_i$.

Confocal Microscopy

To measure mitochondrial ROS, the fluorescent probe MitoSOX™ Red was used according to the manufacturer's protocol. Briefly, three groups of SCN5A cells or rat NVM were studied: untreated cells, the PL group (cells treated with 1 mmol/L pyruvate and 10 mmol/L lactate for 10 min at room temperature, under which condition intracellular NADH level was increased (References 21-23), see "Results" below), and the NAD-PL group (cells incubated with $NAD^+$ for ~6 hours at 37° C. and then treated with 1 mmol/L pyruvate and 10 mmol/L lactate for 10 min at room temperature). The three groups of cells were then incubated with 2.5 μM MitoSOX™ Red in Hank's balanced salt solution (HBSS) for 10 min at 37° C., followed by three times wash with warm HBSS. Before treatment with MitoSOX™ Red, cells were first stained with Hoechst 33342 (0.4 μg/ml working concentration) for 20 min at 37° C. Images were taken on a Zeiss LSM510 META confocal microscope (Carl Zeiss GmbH, Oberkochen, Germany) using an argon laser excitation (514 nm) with emission collection at more than 560 nm (red). The cell area was calculated, and the whole cell fluorescence of MitoSOX™ Red was measured with ImageJ software. The number of pixels of cell fluorescence divided by the cell area was used to determine the mitochondrial ROS generation. For each of the groups, 9 to 16 cells were used. NADH in water has an emission peak at 460 nm and less than 20% of the maximum value above 560 nm (Reference 46). Therefore, NADH is unlikely to interfere with the fluorescence of MitoSOX™ Red in our experiments.

To measure the effect of elevated intracellular NADH level on the mitochondrial membrane potential ($\Delta\Psi_m$), the fluorescent membrane-permeant cationic probe TMRM, which is readily sequestered by mitochondria, was applied. SCN5A cells or rat NVM were loaded with TMRM (100 nmol/L) (Reference 24) for 30 min at 37° C. in the dark. Then, cells were washed gently twice and kept with the bath solution used in the patch experiments before being placed on the stage of a Zeiss LSM510 META confocal microscope (35° C.). TMRM was excited at 543 nm with a helium neon laser (3%), and the emission was collected through a 560 nm longpass filter. Images were collected at 30 s intervals for 10 min and then 2 min interval for 30 min. For the PL group, pyruvate and lactate were applied after the first image was taken. The mitochondrial uncoupler carbonyl cyanide 3-chlorophenylhydrazone (CCCP, 10 μmol/L) was incubated for 1 min at 35° C. with cells, which is sufficient to completely depolarize $\Delta\Psi_m$ (Reference 25). Images were then collected every 2 min for 20 min. The resulting fluorescence images were processed using Zeiss LSM510 META software to obtain the time course of the TMRM fluorescence changes.

Statistical Evaluations

Data are shown as the mean±SEM. Determinations of statistical significance were performed with ANOVA with Bonferroni correction for comparisons of multiple means. A value of $P<0.05$ was considered statistically significant.

TABLE 1

Parameters of voltage dependence of steady state activation and inactivation of all groups

| | Voltage dependence of activation | | | Voltage dependence of inactivation | | |
|---|---|---|---|---|---|---|
| | $V_{1/2}$, mV | k, mV | n | $V_{1/2}$, mV | k, mV | n |
| SCN5A | −44.7 ± 0.2 | 5.7 ± 0.1 | 14 | −72.9 ± 0.3 | 6.8 ± 0.2 | 15 |
| +100 μM $[NADH]_i$ | −44.5 ± 0.3 | 5.5 ± 0.2 | 16 | −75.6 ± 0.3# | 7.0 ± 0.3 | 21 |
| +100 μM $[NADH]_i$ + 10 mM $[L-NAME]_i$ | −45.9 ± 0.6 | 6.0 ± 0.5 | 8 | −74.8 ± 0.6 | 9.3 ± 0.5 | 7 |
| +100 μM $[NADH]_i$ + 200 μM $[apocynin]_o$ | −43.2 ± 0.3 | 6.9 ± 0.2 | 14 | −78.5 ± 0.6* | 8.6 ± 0.5 | 14 |
| +100 μM $[NADH]_i$ + 200 μM $[allopurinol]_i$ | −44.1 ± 1.1 | 6.6 ± 0.8 | 13 | −77.5 ± 0.6* | 6.9 ± 0.3 | 11 |
| +100 μM $[NADH]_i$ + 5 μM $[mitoTEMPO]_i$ | −44.1 ± 0.2 | 5.9 ± 0.2 | 11 | −77.4 ± 0.2 | 6.1 ± 0.1 | 9 |
| +100 μM $[NADH]_i$ + 1 μM $[rotenone]_i$ | −45.8 ± 0.4 | 5.2 ± 0.5 | 10 | −78.1 ± 0.3* | 7.6 ± 0.3 | 9 |
| +20 μM $[antimycin A]_i$ | −46.1 ± 0.4 | 5.1 ± 0.3 | 13 | −69.3 ± 0.8# | 6.3 ± 0.3 | 7 |
| +100 μM $[NADH]_i$ + 1 mM $[malonate]_o$ | −45.9 ± 0.4 | 5.9 ± 0.3 | 12 | −75.9 ± 0.2 | 6.6 ± 0.2 | 10 |
| +100 μM $[NADH]_i$ + 10 mM $[azide]_i$ | −46.6 ± 0.6 | 5.5 ± 0.5 | 16 | −79.3 ± 0.2* | 5.0 ± 0.2 | 9 |
| +100 μM $[NADH]_i$ + 300 μM $[5-HD]_i$ | −39.9 ± 0.2* | 6.7 ± 0.1 | 13 | −78.8 ± 0.2* | 5.9 ± 0.2 | 7 |
| +200 μM $[diazoxide]_i$ | −45.1 ± 0.5 | 7.1 ± 0.5 | 11 | −71.0 ± 0.3 | 7.5 ± 0.3 | 5 |
| +100 μM $[NADH]_i$ + 500 μM $[DIDS]_i$ | −45.7 ± 0.3 | 5.1 ± 0.2 | 13 | −79.2 ± 0.2* | 6.2 ± 0.2 | 9 |
| +100 μM $[NADH]_i$ + 0.5 μM $[CsA]_i$ | −41.2 ± 1.0* | 5.3 ± 0.8 | 13 | −75.5 ± 0.5 | 7.0 ± 0.4 | 9 |
| +100 μM $[NADH]_i$ + 50 μM $[PK11195]_i$ | −41.3 ± 0.7* | 5.9 ± 0.5 | 15 | −79.0 ± 0.2* | 6.0 ± 0.2 | 7 |
| +100 μM $[NADH]_i$ + 40 μM $[4'-CD]_i$ | −45.6 ± 0.5 | 6.0 ± 0.4 | 14 | −78.6 ± 0.4* | 7.5 ± 0.4 | 10 |

TABLE 1-continued

Parameters of voltage dependence of steady state activation and inactivation of all groups

| | Voltage dependence of activation | | | Voltage dependence of inactivation | | |
|---|---|---|---|---|---|---|
| | $V_{1/2}$, mV | k, mV | n | $V_{1/2}$, mV | k, mV | n |
| +500 µM [FGIN-1-27]$_i$ | −46.7 ± 0.4 | 5.4 ± 0.3 | 9 | −78.9 ± 0.5# | 8.4 ± 0.5 | 7 |
| +100 µM [NADH]$_i$ + 500 µM [FGIN-1-27]$_i$ | −46.7 ± 0.4 | 5.4 ± 0.3 | 9 | −83.3 ± 0.3* | 7.0 ± 0.2 | 5 |

Data are shown as mean ± SEM, n is sample number. For $V_{1/2}$,
$P < 0.05$ vs. SCN5A, and
*$P < 0.05$ vs. +100 µM [NADH]$_i$.

Results

Sources of ROS Induced by NADH

Since SOD is able to block the effect of NADH (Reference 3), ROS are implicated in the signaling cascade whereby NADH reduces $I_{Na}$. Sources of ROS within a cell include uncoupled NOS, the NAD(P)H oxidases, xanthine oxidase, and mitochondria. By using specific inhibitors, we tested which of these was the source of ROS modulating $I_{Na}$ in response to increased cytosolic NADH.

FIG. 1 shows that apocynin, N$^\omega$-nitro-L-arginine methyl ester (L-NAME), and allopurinol did not affect $I_{Na}$, when they were applied alone in SCN5A cells. When applied with 100 µmol/L NADH, none of these blockers were able to inhibit the NADH effect on reducing cardiac $I_{Na}$. Steady state activation (SSA) was minimally affected by these compounds, and there were physiologically nonsignificant trends for hyperpolarizing shifts in steady state inactivation (SSI) with apocynin and allopurinol in the presence of NADH (Table 1). These experiments indicate that the NAD(P)H oxidases, uncoupled NOS, and xanthine oxidases are not the source of ROS induced by NADH.

MitoTEMPO is a highly positively charged TEMPO derivative that is concentrated in the mitochondria matrix and acts there as a superoxide scavenger (References 26 and 27). MitoTEMPO at 5 µM blocked the NADH effect on reducing $I_{Na}$ but had no effect on $I_{Na}$ when applied alone (FIG. 1). The SSA and SSI were not affected by mitoTEMPO with or without the presence of NADH (Table 1). This implied that the mitochondria were a likely source of ROS induced by increased NADH.

Mitochondrial ROS Generation Induced by Elevated NADH

Figure 2:
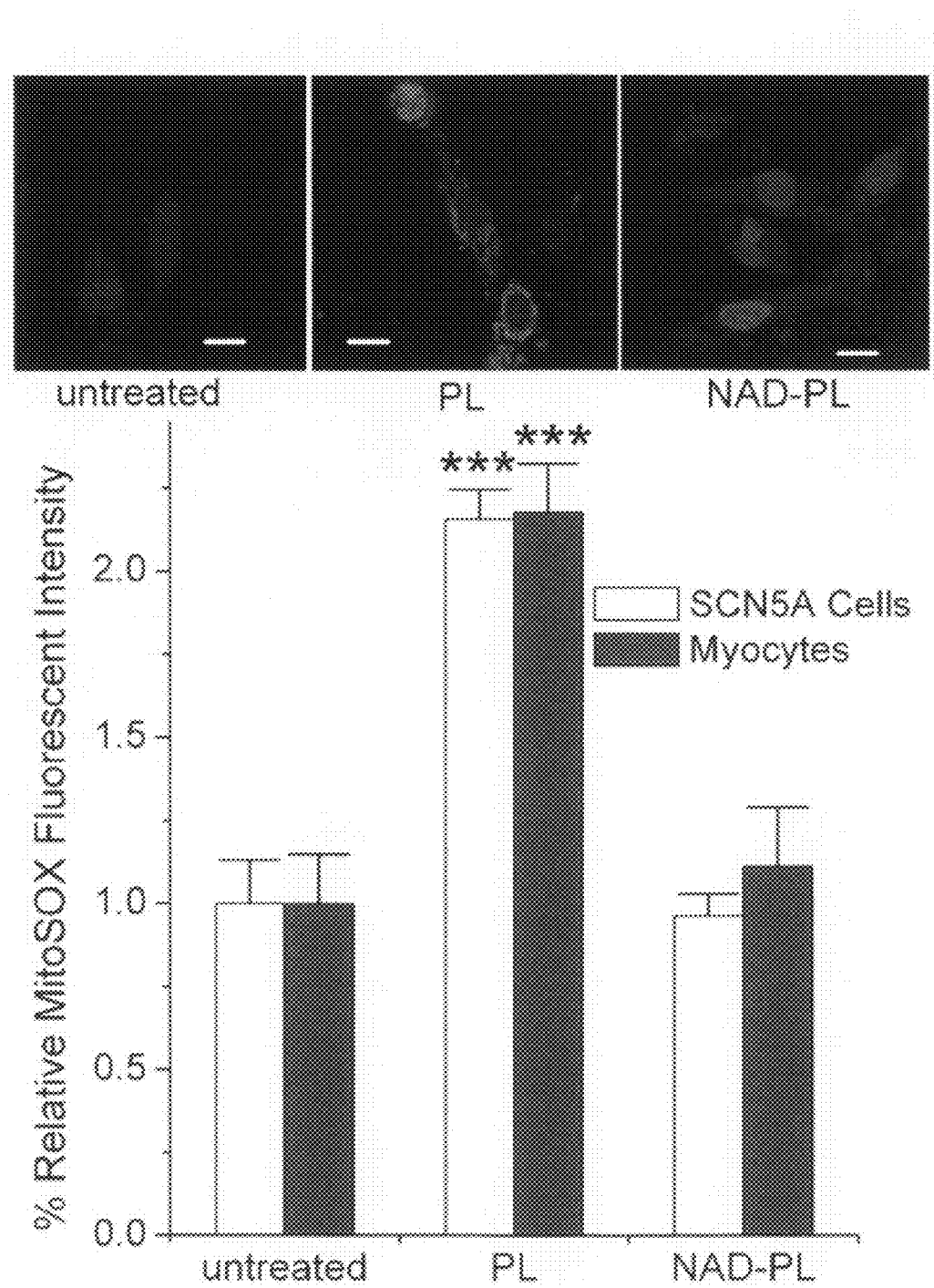
FIG. 2 illustrates mitochondrial ROS production in response to $[NADH]_i$ monitored by MitoSOX™ Red with SCN5A cells and myocytes. The control groups were untreated, the PL groups were treated with 1 and 10 mmol/L pyruvate/lactate for 10 min, and the NAD-PL groups were incubated with 500 µmol/L $NAD^+$ for ~6 hours and then treated with pyruvate/lactate buffer for 10 min. The color pictures in the upper panel are representative images of myocytes of three groups. The scale bar indicates 10 µm. The lower panel shows the relative MitoSOX™ Red fluorescent intensity, ***$P<0.001$ versus the untreated cells or NAD-PL groups. For each group, 9-16 samples were averaged.

Mitochondrial ROS generation was monitored with Mito-SOX™ Red in SCN5A cells and rat NVM, respectively. MitoSOX™ Red is a membrane permeant, fluorogenic dye for selective detection of superoxide in the mitochondria. Once in the mitochondria, the dye is oxidized by superoxide and exhibits red fluorescence. Application of MitoSOX™ Red in untreated cells revealed a low level of red fluorescence, indicating low levels of mitochondrial ROS (FIG. 2). SCN5A cells and rat NVM were treated with 1 and 10 mmol/L PL buffer (PL group in FIG. 2). This PL buffer increased intracellular NADH level by 1.7±0.1-fold and decreased $I_{Na}$ to 0.54±0.04 of control (P<0.01) (Reference 3). Treatments showed 2.06±0.09-fold and 2.18±0.15-fold increases in mitochondrial ROS levels for SCN5A cells and rat NVM as compared to untreated cells, respectively. This increase in ROS was blocked by NAD$^+$ pre-incubation (NAD-PL group in FIG. 2, 0.96±0.06 and 1.11±0.18-fold of untreated cells, respectively). These observations are in agreement with the electrophysiological studies and confirm that mitochondria are the source of ROS overproduction induced by elevated NADH.

The ETC as a Source of NADH-Induced ROS

Figure 3:
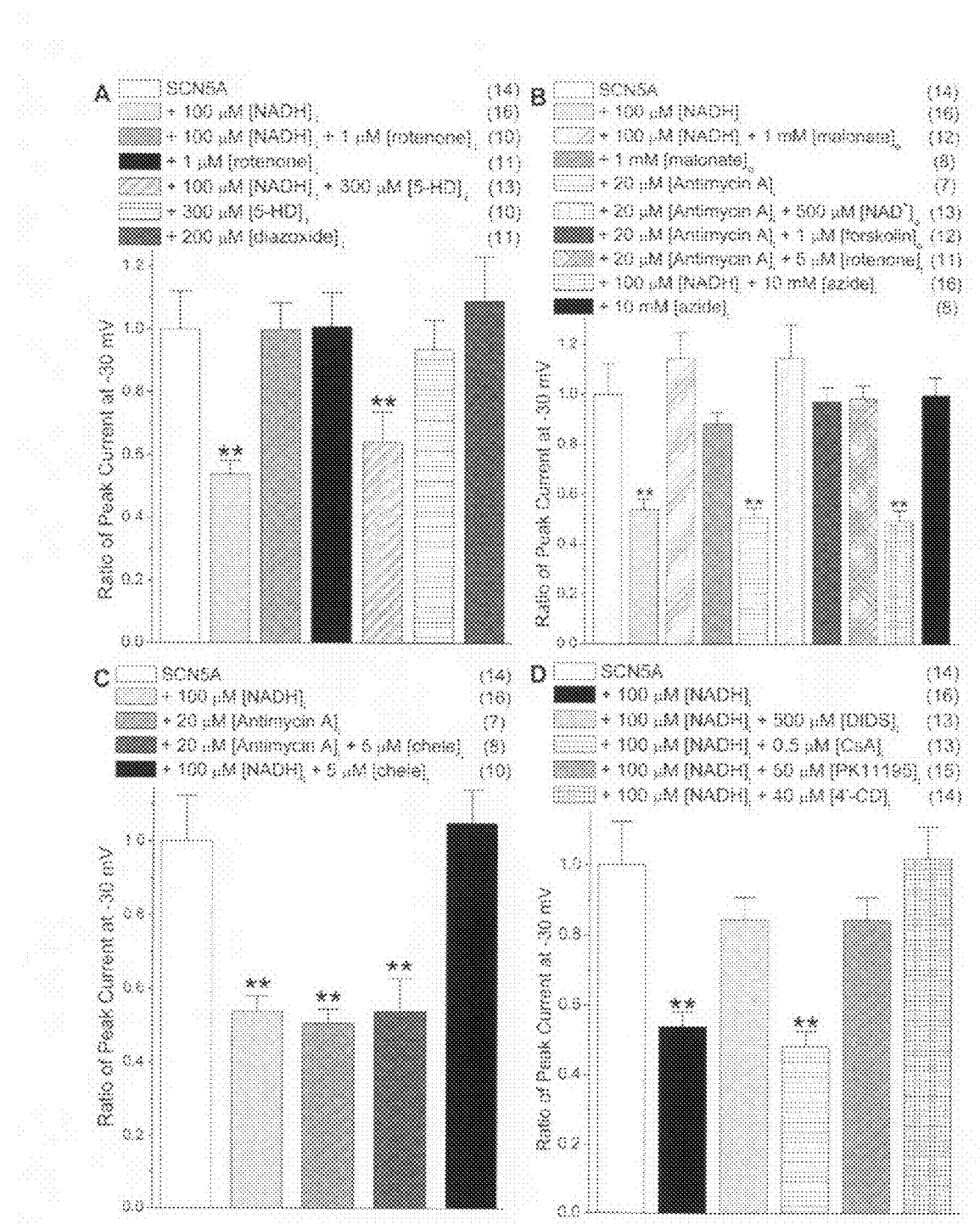
FIG. 3 illustrates that PKC, the electron transport chain, and the IMAC are involved in downregulation of $I_{Na}$ by $[NADH]_i$. (A) Downregulation of $I_{Na}$ by $[NADH]_i$ ($P<0.01$ versus SCN5A) is reversed by rotenone (1 µmol/L), but not by 5-HD. Diazoxide does not affect $I_{Na}$ ($P>0.05$ versus SCN5A). (B) Malonate (1 mmol/L) blocks the NADH effect on reducing $I_{Na}$, and antimycin A (20 µmol/L) reproduces the $[NADH]_i$ effect ($P<0.01$ versus SCN5A group). The antimycin A-induced reduction in $I_{Na}$ is prevented by $[NAD^+]_o$, forskolin, or rotenone. Azide failed to block the NADH effect. (C) Chelerythrine failed to block the antimycin A effect on reducing $I_{Na}$, confirming that PKC activation is required for ROS generation. (D) Downregulation of $I_{Na}$ by $[NADH]_i$ is reversed by DIDS, PK11195 and 4'-CD, but not by CsA (**$P<0.01$ versus SCN5A groups). Numbers in parentheses indicate the number of experiments.
Figure 5:
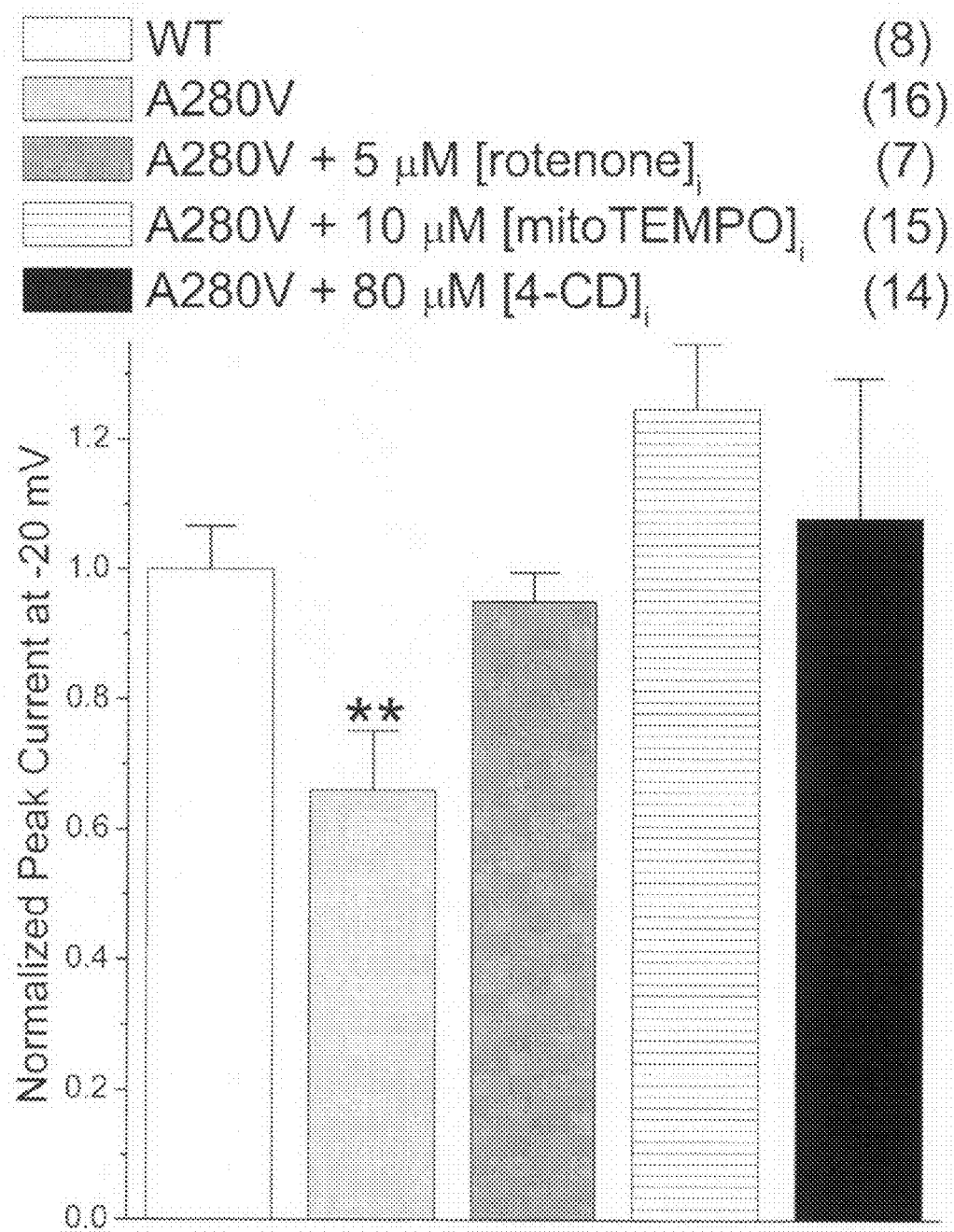
FIG. 5 illustrates downregulation of $I_{Na}$ by A280V GPD1-L being reversed by mitoTEMPO, rotenone, and 4'-CD (**$P<0.01$ versus all other groups). Peak currents at −20 mV were normalized to cell capacitance and divided by the current obtained with SCN5A cells transfected with WT GPD1-L. Numbers in parentheses indicate the number of experiments.

Our previous work has shown that PKC activation is required for ROS production in response to NADH (Reference 3). The ETC and mitochondrial ATP-sensitive K$^+$ channel (mitoK$_{ATP}$) are targets of PKC activation (Reference 28), and both have been shown to be involved in ROS generation and release from mitochondria (References 6, 16, 29 and 30). An inhibitor and an opener of the mitoK$_{ATP}$ channel, 5-hydroxydecanoate (5-HD) (Reference 31) and diazoxide (Reference 32) respectively, were applied to study whether they would have any effect on $I_{Na}$. As shown in FIG. 3A, 5-HD neither blocked the NADH effect on reducing $I_{Na}$ nor showed any effect on $I_{Na}$ when applied alone. Diazoxide did not affect $I_{Na}$, either. For 5-HD, there were minor shifts of $V_{1/2}$ values of the SSA and SSI relationships that were not enough to affect the evaluation of the peak currents (Table 1). These experiments indicate that the mitoK$_{ATP}$ channel is not involved in NADH modulation of Na$_v$1.5.

Complexes I and III are the main sources of ROS production of ETC (References 6, 16 and 33). Rotenone, which decreases ROS generation by inhibiting complex I (i.e. NADH dehydrogenase) (References 6 and 33), blocked entirely the NADH effect on $I_{Na}$ (FIG. 3A), indicating that the ETC was the source of ROS overproduction induced by NADH. Malonate, an inhibitor complex II, (Reference 33) also blocked the NADH effect and reversed the decrease in $I_{Na}$ (FIG. 3B). FIG. 3B also shows that azide, which inhibits complex IV, (Reference 33) failed to block NADH effect on reducing $I_{Na}$. Antimycin A blocks the electron transfer from the Q$_i$ to Q$_o$ sites of complex III and increases ROS generation in the intermembrane space of mitochondria (References 6 and 33). We found that antimycin A gave rise to an equivalent decrease of $I_{Na}$ as did NADH. Comparably to NADH, the antimycin A effect was blocked by NAD$^+$, forskolin, or rotenone as shown in FIG. 3B (Reference 3). A PKC inhibitor, chelerythrine, failed to block the antimycin A effect to reduce $I_{Na}$, as shown in FIG. 3C. This confirmed that PKC activation was necessary for ROS generation from complex III (Reference 3). Shifts of $V_{1/2}$ values of SSI were observed with rotenone and azide in the presence of NADH, and with antimycin A alone. These were minor and unlikely to be sufficient to affect Na$^+$ channel availability significantly at the holding potential used (Table 1).

NADH-Induced ROS Release from Mitochondria was through the Mitochondrial Inner Membrane Anion Channel (IMAC)

Mitochondrial respiration is ordinarily accompanied by low-level ROS generation. In the event of significant cellular ROS, mitochondria respond by increasing their own ROS production, a phenomenon termed ROS-induced ROS release (RIRR) (References 34 and 35). Two modes of RIRR have been reported: the mitochondrial inner membrane anion channel (IMAC)-dependent and the mitochondrial permeability transition pore (MPTP)-dependent mechanisms.

These two anions channels along with the voltage-dependent anion channel (VDAC) are thought to be the predominant paths for cytosolic release of superoxide generated by the ETC. Cycloporine A (CsA) and 4,4'-diisothiocyanatostilbene-2,2'-disulfonic acid (DIDS) are inhibitors of MPTP and IMAC/VDAC, respectively. FIG. 3D shows that DIDS blocked the NADH effect on reducing $I_{Na}$, but CsA did not. Measurements of the mitochondrial $\Delta\Psi_m$ with TMRM showed that elevated NADH levels did not affect the $\Delta\Psi_m$ (data not shown). This indicated that the IMAC or VDAC but not MPTP are involved in ROS release in response to NADH.

IMAC is regulated by the mitochondrial benzodiazepine receptor (mBzR). It has been reported that ROS generation and oscillations are prevented by inhibiting IMAC with mBzR ligands such as 4'-chlorodiazepam (4'-CD) and PK11195 (Reference 6). Inhibition of mitochondria ROS release by 4'-CD is thought to prevent reperfusion arrhythmias (Reference 24). As shown in FIG. 3D, both 4'-CD and PK11195 were capable of blocking the NADH effect on $I_{Na}$. Since the mBzR modifies ROS release through the IMAC, these data strengthen the idea that IMAC is involved in mitochondrial ROS release in response to NADH. FGIN-1-27 (500 μmol/L), an activator of mBzR (References 6 and 24), showed that simply opening the mBzR was not enough to decrease $I_{Na}$ (1.01±0.14 of SCN5A group, P>0.05). When FGIN-1-27 and NADH were applied together, FGIN-1-27 showed no influence on the reduction in $I_{Na}$ mediated by NADH. NADH (100 μmol/L) alone reduced $I_{Na}$ to 0.54±0.04 of SCN5A group (P<0.01) (Reference 3), while in the presence of FGIN-1-27 (500 μmol/L), the reduction of $I_{Na}$ by NADH was 0.51±0.04 (P<0.01). This implies that the mBzR is fully activated in the presence of NADH.

Neonatal Ventricular Myocytes Show Similar Results

Figure 4:
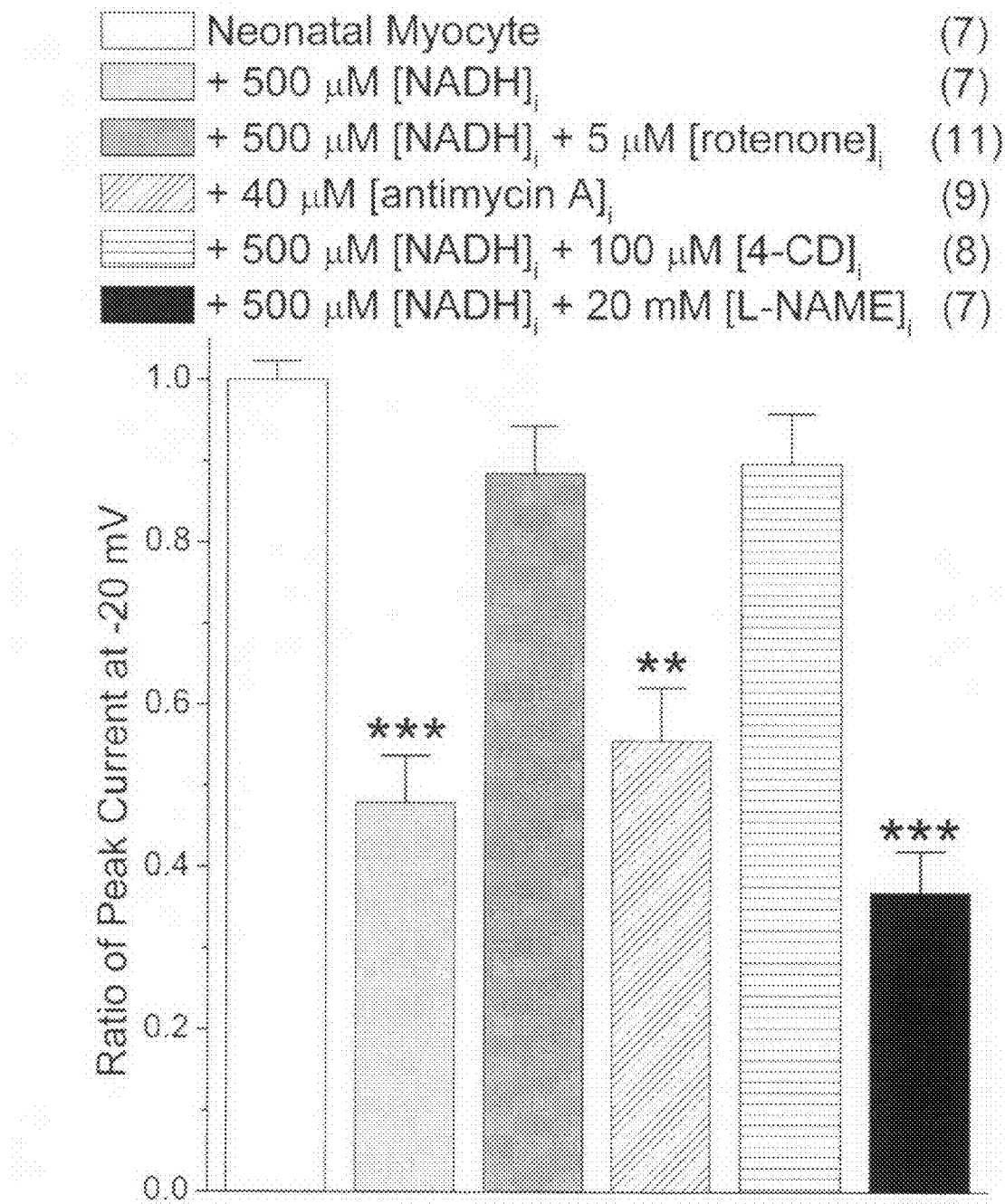
FIG. 4 illustrates neonatal ventricular myocytes analogous downregulation of $I_{Na}$ by $[NADH]_i$. Downregulation can be blocked by rotenone and 4'-CD, but not L-NAME. Antimycin A decreases $I_{Na}$ similarly to that of $[NADH]_i$ ($P<0.01$ and *$P<0.001$ versus control myocytes). Numbers in parentheses indicate the number of experiments.

Analogous experiments were repeated using rat NVM to confirm the effects of rotenone, antimycin A, 4'-CD, and L-NAME on NADH regulation of $Na_v1.5$. As shown in FIG. 4, rotenone and 4'-CD blocked the NADH effect on $I_{Na}$, while L-NAME did not. Antimycin A reduced $I_{Na}$ to 55±7% in myocytes. These results were in agreement with the findings obtained with SCN5A cells, confirming the mitochondrial role on NADH regulation of $Na_v1.5$ in myocytes.

NADH treatment did not affect the maximum diastolic membrane potential. The value for untreated NVM was −66.9±1.4 mV and was −64.3±1.8 mV for myocytes treated with 500 μmol/L NADH (p=NS). On the other hand, treatment with NADH decreased the maximum upstroke velocity of the action potential to 0.68±0.12 of untreated NVM (P<0.05).

A280V GPD1-L and NADH Affect $I_{Na}$ Correspondingly

Previously, we have found that the mutant A280V GPD1-L reduces $I_{Na}$ by increasing intracellular NADH (Reference 3). Similarly to the NADH-mediated $I_{Na}$ reduction, mitoTEMPO, rotenone, and 4'-CD all reversed the $I_{Na}$ decrease caused by A280V GPD1-L (FIG. 5). When these compounds were applied to cells expressing WT GPD1-L, the $I_{Na}$ was unvaried (data not shown). These results imply that increased NADH mediates the effect of A280V GPD1-L to downregulate $Na_v1.5$ and that mitochondrial ETC and IMAC are involved in the pro-arrhythmic effect of this mutation.

Discussion

Many signaling pathways involved in cardiomyopathy and cardioprotection converged on the mitochondria. Mitochondria comprise ~30-40% of the myocyte volume and generate >90% of the ATP (References 36 and 37). Also, they are a major site of physiological ROS production in the cardiomyocyte, with 1-3% of the electrons flowing through the ETC leaking to produce ROS (References 38 and 39). ROS generation within the mitochondrial matrix depends critically on the proton motive force, the NADH/NAD$^+$ ratio, the CoQH$_2$/CoQ ratio, and the local $O_2$ concentration. Under conditions of a high NADH/NAD$^+$ ratio, complex I and perhaps other enzymes linked to the NADH pool may contribute to ROS production (Reference 40).

In the present study, we discovered that the oxidative stress induced by NADH is derived from mitochondria. Experiments with different inhibitors for the uncoupled NOS, NAD(P)H oxidases, xanthine oxidases, mitoK$_{ATP}$, and the ETC revealed that the mitochondrial ETC plays a critical role in NADH regulation of $Na_v1.5$. Blockade of the NADH effect to reduce $I_{Na}$ was observed with rotenone and malonate, complex I and II blockers, respectively. Because malonate inhibited the NADH-induced ROS, but cannot prevent ROS release from complex I, it seemed likely that complex III was the source of ROS in our study. Another possibility is reverse electron transfer from complex II to complex I can also lead to ROS production (Reference 41). This is also blocked by malonate and rotenone. Antimycin A inhibits complex III at the Q$_i$ center and increases superoxide generation from the Q$_o$ center (Reference 42). In the present study, antimycin A caused a significantly reduced $I_{Na}$, supporting the idea that complex III is the source of ROS induced by NADH. At the same time, the antimycin A effect could be blocked by NAD$^+$, forskolin, and rotenone. These results are comparable to the inhibition of the NADH effect on $I_{Na}$ reported in this and previous work (Reference 3). Taken together, the data suggest that complex III is the main source of NADH-induced ROS generation and that blockade of electron flow upstream of complex III minimizes ROS production induced by NADH.

ROS produced by leakage of electrons from the ETC can trigger the opening of the mitochondrial IMAC and subsequent release of $O_2.^-$ to the cytoplasm (References 6 and 34). IMAC-dependent ROS release is regulated by the mBzR. Localized mitochondrial ROS release can propagate throughout cardiac cells in the form of oscillations or waves (References 6 and 34). Mitochondrial depolarization associated with increase ROS and activation of the MPTP has been correlated with opening of the mitoK$_{ATP}$ channel and conduction block, referred to as a metabolic sink (Reference 43). We show a second possible mechanism for conduction impairment involving mitochondrial ROS, ROS induced decreased $I_{Na}$, which is dependent on the mBzR and IMAC but not the MPTP. CsA failed to block the NADH effect on reducing $I_{Na}$ while PK11195 and 4'-CD inhibited the NADH effect. This suggests that Na$^+$ channel-mediated changes in conduction may precede those of mitoK$_{ATP}$, since the mitoK$_{ATP}$ effect requires mitochondrial MPTP activation and mitochondrial depolarization whereas the NADH effect requires less extreme mitochondrial ROS production.

Studies of metabolic stress in isolated cardiac cells reveal that energy-sensitive K$^+$ channels in the sarcolemmal membrane can be activated spontaneously in an oscillatory manner (Reference 44). These K$^+$ current oscillations are closely associated with whole cell metabolic oscillations. Modulation of the cellular action potential by these metabolic oscillations could result in arrhythmias in the heart after ischemia-reperfusion. Mitochondria have been identified as the source of the oscillations. K$^+$ channel opening compounds like diazoxide and nicorandil have been found to protect heart cells from ischemic or oxidative stress through a mechanism that involves the opening of mitoK$_{ATP}$ channel (Reference 32). In our work, the blocker for mitoK$_{ATP}$, 5-HD, was unable to protect against the NADH-mediated reduction in $I_{Na}$, and an opener of mitoK$_{ATP}$, diazoxide, did not affect I$_{Na}$, either. These results indicate that the NADH effect is unique and independent of mitoK$_{ATP}$.

Figure 6:
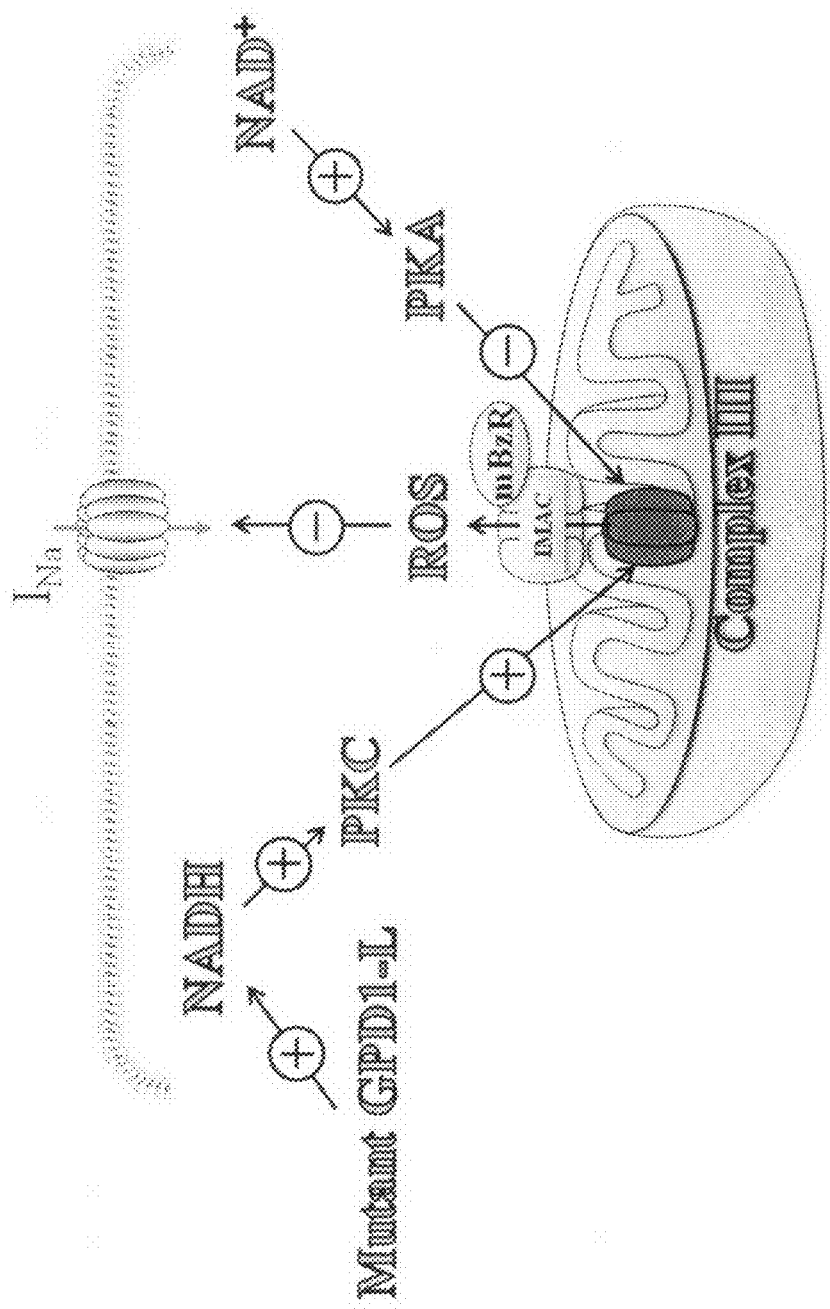
FIG. 6 illustrates a proposed signaling pathway by which the mutant GPD1-L and NADH downregulate cardiac $Na^+$ channel by causing PKC activation and ROS overproduction from the complex III of mitochondrial electron transport chain. Reactive oxygen species (ROS) are released from the mitochondria by the IMAC that is modulated by the mBzR. $NAD^+$ upregulates the cardiac $Na^+$ channel through PKA activation and inhibition of ROS overproduction.

In summary, elevated intracellular NADH leads to mitochondrial ROS overproduction that results in downregulation of the cardiac Na$^+$ channel. Mitochondrial ROS overproduction is mainly derived from complex III of the electron transport chain, and ROS is probably released into the cytoplasm through the IMAC, which is regulated by the mBzR (FIG. 6). A similar mechanism likely explains the arrhythmia syndromes induced by mutant GPD1-L protein (References 1 and 3), since the mutant GPD1-L A280V leads to an increase of intracellular NADH level and mitoTEMPO, rotenone, and 4'-CD block the A280V GPD1-L effect to reduce I$_{Na}$. Valdivia et al. (Reference 45) presented a somewhat different possible signaling pathway to explain the reduction in I$_{Na}$ with mutations of GPD1-L. Nevertheless, the two proposals share many elements, including elevated NADH and PKC activation being involved in the signaling cascade. In experiments not shown, the lack of effect on I$_{Na}$ of raising intracellular dihydroxyacetone phosphate, which should increase glycerol-3-phosphate production by glycerol-3-phosphate dehydrogenase catalysis without raising NADH levels, suggests that NADH and not glycerol-3-phosphate is mediating the reduction in current.

Our experiments do not unequivocally establish a mechanism by which mitochondrial ROS reduce I$_{Na}$. ROS could be having a direct effect on the channel, cause the channel to be excluded from the membrane, or alter channel post-translational modifications known to decrease I$_{Na}$. Preliminary experiments suggest that the disulfide reducing agent, dithiothreitol, does not prevent the NADH effect. Moreover, preliminary total internal reflection fluoroscopy experiments with labeled sodium channels do not show any channel internalization in response to NADH. It seems reasonable that PKC acts directly on the channel, as proposed by Valdivia et al. (Reference 45). Changes in the SSA and SSI relationships support this assertion. It is interesting to note, however, that the effect of only one of two GPD1-L mutations known to cause sudden death is fully reversed by eliminating a Na$^+$ channel PKC phosphorylation site, suggesting the possibility of multiple mechanisms or sites being involved in the current reduction. Our results represent a heretofore unknown regulation of the cardiac Na$^+$ channel by NADH through mitochondria ROS production that may help explain the link between altered metabolism and arrhythmic risk.

The following is a list of abbreviation and acronyms used herein:
4'-CD, 4'-chlorodiazepam
5-HD, 5-hydroxydecanoate
AP, action potential
CCCP, carbonyl cyanide 3-chlorophenylhydrazone
CsA, Cyclorporine A
DIDS, 4'-diisothiocyanatostilbene-2,2'-disulfonic acid
ETC, electron transport chain
FGIN-1-27, [N,N-dihexyl-2-(4-fluorophenyl)indole-3-acetamide
GFP, green fluorescent protein
GPD1-L, glycerol-3-phosphate dehydrogenase 1-like
HEK, human embryonic kidney
IMAC, the mitochondrial inner membrane anion channel
L-NAME, N$^{\omega}$-nitro-L-arginine methyl ester
mBzR, the mitochondrial benzodiazepine receptor
mitoK$_{ATP}$, mitochondrial ATP-sensitive K$^+$ channel
MPTP, the mitochondrial permeability transition pore
Na$_v$1.5, cardiac sodium channel
NOS, nitric oxide synthase
NVM, neonatal ventricular myocyte
PK, protein kinase
PL, pyruvate/lactate
RFP, red fluorescent protein
RIRR, ROS-induced ROS release
SCN5A, cardiac sodium channel
SOD, superoxide dismutase
SSA, steady state activation
SSI, steady state inactivation
TMRM, tetramethylrhodamine methyl ester
VDAC, the voltage-dependent anion channel While this invention has been described as having preferred sequences, ranges, steps, materials, structures, components, features, and/or designs, it is understood that it is capable of further modifications, uses, and/or adaptations of the invention following in general the principle of the invention, and including such departures from the present disclosure as those come within the known or customary practice in the art to which the invention pertains, and as may be applied to the central features hereinbeforesetforth, and fall within the scope of the invention and of the limits of the appended claims.

REFERENCES

The following references, and any cited in the disclosure herein, are hereby incorporated herein in their entirety by reference.

(1) London B, Michalec M, Mehdi H, Zhu X, Kerchner L, Sanyal S, Viswanathan P C, Pfahnl A E, Shang L L, Madhusudanan M, Baty C J, Lagana S, Aleong R, Gutmann R, Ackerman M J, McNamara D M, Weiss R, Dudley S C, Jr. Mutation in glycerol-3-phosphate dehydrogenase 1-like gene (GPD1-L) decreases cardiac Na$^+$ current and causes inherited arrhythmias. *Circulation.* 2007; 116:2260-8.

(2) Van Norstrand D W, Valdivia C R, Tester D J, Ueda K, London B, Makielski J C, Ackerman M J. Molecular and functional characterization of novel glycerol-3-phosphate dehydrogenase 1 like gene (GPD1-L) mutations in sudden infant death syndrome. *Circulation.* 2007; 116:2253-9.

(3) Liu M, Sanyal S, Gao G, Gurung I S, Zhu X, Gaconnet G, Kerchner L J, Shang L L, Huang C L H, Grace A, London B, Dudley S C, Jr. Cardiac Na$^+$ current regulation by pyridine nucleotides. *Circ Res.* 2009; 105:737-45.

(4) Shaw R M, Rudy Y. Ionic mechanisms of propagation in cardiac tissue: roles of the sodium and L-type calcium currents during reduced excitability and decreased gap junction coupling. *Circ Res.* 1997; 81:727-41.

(5) Shimizu W, Aiba T, Kamakura S. Mechanisms of disease: current understanding and future challenges in Brugada syndrome. *Nat Clin Pract Cardiovasc Med.* 2005; 2:408-14.

(6) Aon M A, Cortassa S, Marban E, O'Rourke B. Synchronized whole cell oscillations in mitochondrial metabolism triggered by a local release of reactive oxygen species in cardiac myocytes. *J Biol Chem.* 2003; 278:44735-44.

(7) Di L F, Menabo R, Canton M, Barile M, Bernardi P. Opening of the mitochondrial permeability transition pore causes depletion of mitochondrial and cytosolic NAD$^+$ and is a causative event in the death of myocytes in postischemic reperfusion of the heart. *J Biol Chem.* 2001; 276: 2571-5.

(8) Choudhary G, Dudley S C, Jr. Heart failure, oxidative stress, and ion channel modulation. *Congest Heart Fail.* 2002; 8:148-55.

(9) Pillai J B, Isbatan A, Imai Si, Gupta M P. Poly(ADP-ribose) polymerase-1-dependent cardiac myocyte cell death during heart failure is mediated by NAD$^+$ depletion and reduced Sir2a deacetylase activity. *J Biol Chem.* 2005; 280:43121-30.

(10) Dzhanashiya P K, Vladytskaya O V, Salibegashvili N V. Efficiency and mechanisms of the antioxidant effect of standard therapy and refracterin in the treatment of chronic heart failure in elderly patients with postinfarction cardiosclerosis. *Bull Exp Biol Med.* 2004; 138:412-4.

(11) Makielski J C, Farley A. Na$^+$ current in human ventricle: implications for sodium loading and homeostasis. *J Cardiovasc Electrophysiol.* 2006; 17:S15-S20.

(12) Valdivia C R, Chu V V W, Pu J, Foell J D, Haworth R A, Wolff M R, Kamp T J, Makielski J C. Increased late sodium current in myocytes from a canine heart failure model and from failing human heart. *J Mol Cell Cardiol.* 2005; 38:475-83.

(13) Silberman G A, Fan T-H, Liu H, Jiao Z, Xiao H D, Lovelock J D, Boulden B, Widder J, Fredd S, Bernstein K E, Wolska B, Dikalov S, Harrison D G, Dudley S C Jr. Uncoupled cardiac nitric oxide synthase mediates diastolic dysfunction. *Circulation.* 2010; 121:519-28.

(14) Sorescu D, Weiss D, Lassegue B, Clempus R E, Szocs K, Sorescu G P, Valppu L, Quinn M T, Lambeth J D, Vega J D, Taylor W R, Griendling K K. Superoxide production and expression of Nox family proteins in human atherosclerosis. *Circulation.* 2002; 105:1429-35.

(15) Pacher P, Nivorozhkin A, Szabo C. Therapeutic effects of xanthine oxidase inhibitors: Renaissance half a century after the discovery of allopurinol. *Pharmacol Rev.* 2006; 58:87-114.

(16) Andrukhiv A, Costa A D T, West I, Garlid K D. Opening of mitoK$_{ATP}$ increases superoxide generation from complex I of the electron transport chain. *Am J Physiol Heart Circ Physiol.* 2006; 291:H2067-H2074.

(17) Ide T, Tsutsui H, Kinugawa S, Utsumi H, Kang D, Hattori N, Uchida K, Arimura Ki, Egashira K, Takeshita A. Mitochondrial electron transport complex I is a potential source of oxygen free radicals in the failing myocardium. *Circ Res.* 1999; 85:357-63.

(18) Mallat Z, Philip I, Lebret M, Chatel D, Maclouf J, Tedgui A. Elevated levels of 8-iso-prostaglandin F2a in pericardial fluid of patients with heart failure: a potential role for in vivo oxidant stress in ventricular dilatation and progression to heart failure. *Circulation.* 1998; 97:1536-9.

(19) Hill M F, Singal P K. Right and left myocardial antioxidant responses during heart failure subsequent to myocardial infarction. *Circulation.* 1997; 96:2414-20.

(20) Dhalla A K, Singal P K. Antioxidant changes in hypertrophied and failing guinea pig hearts. *Am J Physiol Heart Circ Physiol.* 1994; 266:H1280-H1285.

(21) Kobayashi K, Neely J R. Control of maximum rates of glycolysis in rat cardiac muscle. *Circ Res.* 1979; 44:166-75.

(22) Li Q, Hwang Y C, Ananthakrishnan R, Oates P J, Guberski D, Ramasamy R. Polyol pathway and modulation of ischemia-reperfusion injury in Type 2 diabetic BBZ rat hearts. *Cardiovasc Diabetol.* 2008; 7:33-44.

(23) Moir A M, Zammit V A. Insulin-independent and extremely rapid switch in the partitioning of hepatic fatty acids from oxidation to esterification in starved-refed diabetic rats. *Biochem J.* 1995; 305:953-8.

(24) Akar F G, Aon M A, Tomaselli G F, O'Rourke B. The mitochondrial origin of postischemic arrhythmias. *J Clin Invest.* 2005; 115:3527-35.

(25) van Raam B, Sluiter W, de Wit E, Roos D, Verhoeven A, Kuijpers T. Mitochondrial membrane potential in human neutropils is maintained by complex III activity in the absence of supercomplex organisation. *PLoS ONE.* 2008; 3:e2013.

(26) Liang H L, Arsenault J, Mortensen J, Park F, Johnson C P, Nilakanta V. Partial attenuation of cytotoxicity and apoptosis by SOD1 in ischemic renal epithelial cells. *Apoptosis.* 2009; 14:1176-89.

(27) Dikalova A E, Bikineyeva A T, Budzyn K, Nazarewicz R R, McCann L, Lewis W, Harrison D G, Dikalov S I. Therapeutic targeting of mitochondrial superoxide in hypertension. *Circ Res.* 2010; 107:106-16.

(28) Budas G, Mochly-Rosen D. Mitochondrial protein kinase Ce (PKCe): emerging role in cardiac protection from ischaemic damage. *Biochem Soc Trans.* 2007; 35:1052-4.

(29) Costa A D T, Pierre S V, Cohen M V, Downey J M, Garlid K D. cGMP signalling in pre- and post-conditioning: the role of mitochondria. *Cardiovasc Res.* 2008; 77:344-52.

(30) Ogbi M, Chew C S, Pohl J, Stuchlik O, Ogbi S, Johnson J A. Cytochrome c oxidase subunit IV as a marker of protein kinase Ce function in neonatal cardiac myocytes: implications for cytochrome c oxidase activity. *Biochem J.* 2004; 382:923-32.

(31) Sato T, O'Rourke B, Marban E. Modulation of mitochondrial ATP-dependent K$^+$ channels by protein kinase C. *Circ Res.* 1998; 83:110-4.

(32) O+Rourke B. Evidence for mitochondrial K$^+$ channels and their role in cardioprotection. *Circ Res.* 2004; 94:420-32.

(33) Chen Q, Vazquez E, Moghaddas S, Hoppel C, Lesnefsky E. Production of reactive oxygen species by mitochondria. *J Biol Chem.* 2003; 278:36027-31.

(34) Brady N, Hamacher-Brady A, Westerhoff H, Gottlieb R. A wave of reactive oxygen species (ROS)-induced ROS release in a sea of excitable mitochondria. *Antioxid Redox Signal.* 2006; 8:1651-65.

(35) Zorov D B, Filburn C R, Klotz L O, Zweier J L, Sollott S J. Reactive oxygen species (ROS)-induced ROS release: a new phenomenon accompanying induction of the mitochondrial permeability transition in cardiac myocytes. *J Exp Med.* 2000; 192:1001-14.

(36) Murphy E, Steenbergen C. Preconditioning: the mitochondrial connection. *Annu Rev Physiol.* 2007; 69:51-67.

(37) Barth E, Stämmler G, Speiser B, Schaper J. Ultrastructural quantitation of mitochondria and myofilaments in cardiac muscle from 10 different animal species including man. *J Mol Cell Cardiol.* 1992; 24:669-81.

(38) Boveris A, Oshino N, Chance B. The cellular production of hydrogen peroxide. *Biochem J.* 1972; 128:617-31.

(39) Batandier C, Fontaine E, Keriel C, Leverve X. Determination of mitochondrial reactive oxygen species: methodological aspects. *J Cell Mol Med.* 2002; 6:175-87.

(40) Murphy M P. How mitochondria produce reactive oxygen species. *Biochem J.* 2009; 417:1-13.

(41) Panov A, Schonfeld P, Dikalov S, Hemendinger R, Bonkovsky H L, Brooks B R. The Neuromediator glutamate, through specific substrate interactions, enhances mitochondrial ATP production and reactive oxygen species generation in monsynaptic brain mitochondria. *J Biol Chem.* 2009; 284:14448-56.

(42) Han D, Antunes F, Canali R, Rettori D, Cadenas E. Voltage-dependent anion channels control the release of the superoxide anion from mitochondria to cytosol. *J Biol Chem.* 2003; 278:5557-63.

(43) Brown D, Aon M A, Akar F G, Liu T, Sorarrain N, O'Rourke B. Effects of 4'-chlorodiazepam on cellular excitation-constraction coupling and ischaemia-reperfusion injury in rabbit heart. *Cardiovasc Res.* 2008; 79:141-9.
(44) O'Rourke B, Ramza B, Marban E. Oscillations of membrane current and excitability driven by metabolic oscillations in heart cells. *Science.* 1994; 265:962-6.
(45) Valdivia C R, Ueda K, Ackerman M J, Makielski J C. GPD1L links redox state to cardiac excitability by PKC-dependent phosphorylation of the sodium channel SCN5A. *AJP—Heart and Circulatory Physiology.* 2009; 297:H1446-H1452.
(46) Zelent B, Troxler T, Vanderkooi J M. Temperature dependence for fluorescence of β-NADH in glycerol/water solution and in trehalose/sucrose glass. *Journal of Fluorescence.* 2007; 17:37-42.
(47) Liu M, Gaconnet G, London B, Dudley, Jr. S. C. A Central Role of Mitochondria in the Regulation of Sodium Current. Presentation at the Cardiac Electrophysiology Society, Orlando, Fla. (Nov. 14, 2009) (1 page).

What is claimed is:

1. A method of reducing arrhythmic risk in an individual with elevated intracellular NADH level, comprising the steps of:
a) providing an individual with elevated intracellular NADH level;
b) lowering the intracellular NADH level to a predetermined normal level by administering to the individual a therapeutic amount of a mitochondrial targeted antioxidant; and
c) wherein achieving the normal intracellular NADH level reduces arrhythmic risk in the individual.

2. The method of claim 1, wherein the amount of antioxidant is effective to reduce arrhythmic risk.

3. The method of claim 1, wherein the antioxidant prevents reduction in sodium channel current ($I_{Na}$) by reducing or suppressing mitochondrial ROS production.

4. The method of claim 1, wherein the antioxidant is administered orally or intravenously.

5. The method of claim 1, wherein the individual is suffering from arrhythmia.

6. The method of claim 1, wherein the antioxidant comprises at least one member selected from the group consisting of a powder, a tablet, a capsule, a solution, a suspension, and an injectable formulation.

7. The method of claim 1, wherein the antioxidant prevents a change in sodium channel current ($I_{Na}$) by reducing or suppressing mitochondrial ROS production.

* * * * *